United States Patent
Rai et al.

(10) Patent No.: US 6,369,011 B1
(45) Date of Patent: Apr. 9, 2002

(54) PROTEASE ENZYMES FOR TOUGH CLEANING AND/OR SPOT AND FILM REDUCTION AND COMPOSITIONS INCORPORATING SAME

(75) Inventors: Saroj Rai, Round Rock, TX (US); Paul Elliott Correa; Yong Zhu, both of Cincinnati, OH (US); Thomas Paul Graycar, Pacifica; Richard Ray Bott, Burlingame, both of CA (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/445,270

(22) PCT Filed: Jun. 2, 1998

(86) PCT No.: PCT/IB98/00853

§ 371 Date: Mar. 3, 2000

§ 102(e) Date: Mar. 3, 2000

(87) PCT Pub. No.: WO98/55634

PCT Pub. Date: Dec. 10, 1998

Related U.S. Application Data

(60) Provisional application No. 60/048,550, filed on Jun. 4, 1997.

(51) Int. Cl.[7] .............................. C11D 7/42; C11D 7/18; C11D 7/54

(52) U.S. Cl. ...................... 510/221; 510/226; 510/305; 510/306; 510/308; 510/320; 510/321; 510/392; 510/393; 510/530

(58) Field of Search .................................. 510/220, 221, 510/226, 305, 306, 308, 320, 321, 392, 393, 530; 8/137, 130

(56) References Cited

U.S. PATENT DOCUMENTS 5,962,386 A * 10/1999 Scheper et al. ............. 510/221

FOREIGN PATENT DOCUMENTS

| WO | WO 89/06270 | 7/1989 | ........... C11D/3/386 |
|---|---|---|---|
| WO | 95/10591 | * 4/1995 | |
| WO | 95/10615 | * 4/1995 | |

OTHER PUBLICATIONS

Kirk–Othmer, Encyclopedia of Chemical Technology, Fourth Edition, vol. 9, pp. 567–620, *Enzyme Applications (Industrial)*, Peder Holk Nielsen et al.

* cited by examiner

Primary Examiner—Gregory Delcotto
(74) Attorney, Agent, or Firm—Kevin L. Waugh; Kim William Zerby; Steven W. Miller

(57) ABSTRACT

The present relates to cleaning compositions comprising a protease enzyme which is a carbonyl variant having an amino acid sequence not found in nature, which is derived by replacement of a plurality of amino acid residues of a precursor carbonyl ydrolase with different amino acids.

11 Claims, 10 Drawing Sheets

```
              10                  30                  50
ATGAAGAAACCGTTGGGGAAAATTGTCGCAAGCACCGCACTACTCATTTCTGTTGCTTTT
MetLysLysProLeuGlyLysIleValAlaSerThrAlaLeuLeuIleSerValAlaPhe 70                  90                 110
AGTTCATCGATCGCATCGGCTGCTGAAGAAGCAAAAGAAAAATATTTAATTGGCTTTAAT
SerSerSerIleAlaSerAlaAlaGluGluAlaLysGluLysTyrLeuIleGlyPheAsn 130                 150                 170
GAGCAGGAAGCTGTCAGTGAGTTTGTAGAACAAGTAGAGGCAAATGACGAGGTCGCCATT
GluGlnGluAlaValSerGluPheValGluGlnValGluAlaAsnAspGluValAlaIle 190                 210                 230
CTCTCTGAGGAAGAGGAAGTCGAAATTGAATTGCTTCATGAATTTGAAACGATTCCTGTT
LeuSerGluGluGluGluValGluIleGluLeuLeuHisGluPheGluThrIleProVal 250                 270                 290
TTATCCGTTGAGTTAAGCCCAGAAGATGTGGACGCGCTTGAACTCGATCCAGCGATTTCT
LeuSerValGluLeuSerProGluAspValAspAlaLeuGluLeuAspProAlaIleSer 310                 330                 350
TATATTGAAGAGGATGCAGAAGTAACGACAATGGCGCAATCAGTGCCATGGGGAATTAGC
TyrIleGluGluAspAlaGluValThrThrMetAlaGlnSerValProTrpGlyIleSer 370                 390                 410
CGTGTGCAAGCCCCAGCTGCCCATAACCGTGGATTGACAGGTTCTGGTGTAAAAGTTGCT
ArgValGlnAlaProAlaAlaHisAsnArgGlyLeuThrGlySerGlyValLysValAla 430                 450                 470
GTCCTCGATACAGGTATTTCCACTCATCCAGACTTAAATATTCGTGGTGGCGCTAGCTTT
ValLeuAspThrGlyIleSerThrHisProAspLeuAsnIleArgGlyGlyAlaSerPhe 490                 510                 530
GTACCAGGGGAACCATCCACTCAAGATGGGAATGGGCATGGCACGCATGTGGCCGGGACG
ValProGlyGluProSerThrGlnAspGlyAsnGlyHisGlyThrHisValAlaGlyThr 550                 570                 590
ATTGCTGCTTTAAACAATTCGATTGGCGTTCTTGGCGTAGCGCCGAGCGCGGAACTATAC
IleAlaAlaLeuAsnAsnSerIleGlyValLeuGlyValAlaProSerAlaGluLeuTyr 610                 630                 650
GCTGTTAAAGTATTAGGGGCGAGCGGTTCAGGTTCGGTCAGCTCGATTGCCCAAGGATTG
AlaValLysValLeuGlyAlaSerGlySerGlySerValSerSerIleAlaGlnGlyLeu 670                 690                 710
GAATGGGCAGGGAACAATGGCATGCACGTTGCTAATTTGAGTTTAGGAAGCCCTTCGCCA
GluTrpAlaGlyAsnAsnGlyMetHisValAlaAsnLeuSerLeuGlySerProSerPro 730                 750                 770
AGTGCCACACTTGAGCAAGCTGTTAATAGCGCGACTTCTAGAGGCGTTCTTGTTGTAGCG
SerAlaThrLeuGluGlnAlaValAsnSerAlaThrSerArgGlyValLeuValValAla 790                 810                 830
GCATCTGGGAATTCAGGTGCAGGCTCAATCAGCTATCCGGCCCGTTATGCGAACGCAATG
AlaSerGlyAsnSerGlyAlaGlySerIleSerTyrProAlaArgTyrAlaAsnAlaMet 850                 870                 890
GCAGTCGGAGCTACTGACCAAAACAACAACCGCGCCAGCTTTTCACAGTATGGCGCAGGG
AlaValGlyAlaThrAspGlnAsnAsnAsnArgAlaSerPheSerGlnTyrGlyAlaGly
```

FIG. 1A

```
            910                    930                    950
CTTGACATTGTCGCACCAGGTGTAAACGTGCAGAGCACATACCCAGGTTCAACGTATGCC
LeuAspIleValAlaProGlyValAsnValGlnSerThrTyrProGlySerThrTyrAla 970                    990                   1010
AGCTTAAACGGTACATCGATGGCTACTCCTCATGTTGCAGGTGCAGCAGCCCTTGTTAAA
SerLeuAsnGlyThrSerMetAlaThrProHisValAlaGlyAlaAlaAlaLeuValLys 1030                   1050                   1070
CAAAAGAACCCATCTTGGTCCAATGTACAAATCCGCAATCATCTAAAGAATACGGCAACG
GlnLysAsnProSerTrpSerAsnValGlnIleArgAsnHisLeuLysAsnThrAlaThr 1090                   1110                   1130
AGCTTAGGAAGCACGAACTTGTATGGAAGCGGACTTGTCAATGCAGAAGCGGCAACACGC
SerLeuGlySerThrAsnLeuTyrGlySerGlyLeuValAsnAlaGluAlaAlaThrArg
```

FIG. 1B

Comparison of subtilisin sequences from:

B.amyloliquefaciens
B.subtilis
B.licheniformis
B.lentus

```
                        10                    20                    30
01 AQSVPYGVSQIKAPALHSQGYTGSNVKVAVIDSGIDSSHP
   AQSVPYGISQIKAPALHSQGYTGSNVKVAVIDSGIDSSHP
   AQTVPYGIPLIKADKVQAQGFKGANVKVAVLDTGIQASHP
   AQSVPWGISRVQAPAAHNRGLTGSGVKVAVLDTGISTHP*

50                    60                    70
41 DLKVAGGASMVPSETNPFQDNNSHGTHVAGTVAALNNSIG
   DLNVRGGASFVPSETNPYQDGSSHGTHVAGTIAALNNSIG
   DLNVVGGASFVAGEAYNT*DGNGHGTHVAGTVAALDNTTG
   DLNIRGGASFVPGEPSTQDGNGHGTHVAGTIAALNNSIG 90                   100                   110
81 VLGVAPSASLYAVKVLGADGSGQYSWIINGIEWAIANNMD
   VLGVAPSASLYAVKVLDSTGSGQYSWIINGIEWAISNNMD
   VLGVAPSVSLYAVKVLNSSGSGSYSGIVSGIEWATTNGMD
   VLGVAPSAELYAVKVLGASGSGSVSSIAQGLEWAGNNGMH 130                   140                   150
121 VINMSLGGPSGSAAALKAAVDKAVASGVVVVAAAGNEGTSG
    VINMSLGGPTGSTALKTVVDKAVSSGIVVAAAAGNEGSSG
    VINMSLGGASGSTAMKQAVDNAYARGVVVVAAAGNSGNSG
    VANLSLGSPSPSATLEQAVNSATSRGVLVVAASGNSGAGS
```

```
                                                    -1 ┐ ┌── MAT                                                                     10
        His  Bal  Ala  His  Ala  Tyr  Ala  Gln  Ser  Val  Pro  Tyr  Gly  Val  Ser  Gln  Ile  Lys  Ala  Pro  Ala  Leu  His  Ser  Gln
399     CAC  GTA  GCA  CAT  GCG  TAC  GCG  CAG  TCC  GTG  CCT  TAC  GGT  GTA  TCA  CAA  ATT  AAA  GCC  CCT  GCT  CTG  CAC  TCT  CAA 20                                                          30                                          40
        Gly  Tyr  Thr  Gly  Ser  Asn  Val  Lys  Val  Ala  Val  Ile  Asp  Ser  Gly  Ile  Asp  Ser  Ser  His  Pro  Asn  Leu  Lys  Val
474     GGC  TAC  ACT  GGA  TCA  AAT  GTT  AAA  GTA  GCG  GTT  ATC  GAC  AGC  GGT  ATC  GAT  TCT  TCT  CAT  CCT  GAT  TTA  AAG  GTA

50                                              Pro  Asn              60 Asp
        Ala  Gly  Gly  Ala  Ser  Met  Val  Pro  Ser  Glu  Thr  Asn  Pro  Phe  Gln  Asp  Asn  Asn  Ser  His  Gly  Thr  His  Val  Ala
549     GCA  GGT  GGA  GCC  AGC  ATG  GTT  CCT  TCT  GAA  ACA  AAT  CCT  TTC  CAA  GAC  AAC  AAC  TCT  CAC  GGA  ACT  CAC  GTT  GCC 70                                                              80                      Ser  Ala  90
        Gly  Thr  Val  Ala  Ala  Leu  Asn  Asn  Ser  Ile  Gly  Val  Leu  Gly  Val  Ala  Pro  Ser  Ala  Ser  Leu  Tyr  Ala  Val  Lys
624     GGC  ACA  GTT  GCG  GCT  CTT  AAT  AAC  TCA  ATC  GGT  GTA  TTA  GGC  GTT  GCG  CCA  AGC  GCA  TCA  CTT  TAC  GCT  GTA  AAA

Asp  Ala 100                                                110
        Val  Leu  Gly  Ala  Asp  Gly  Ser  Gly  Gln  Tyr  Ser  Trp  Ile  Ile  Asn  Gly  Ile  Glu  Trp  Ala  Ile  Ala  Asn  Asn  Met
699     GTT  CTC  GGT  GCT  GAC  GGT  TCC  GGC  CAA  TAC  AGC  TGG  ATC  ATT  AAC  GGA  ATC  GAG  TGG  GCG  ATC  GCA  AAC  AAT  ATG 120                                                         130                                         140
        Asp  Val  Ile  Asn  Met  Ser  Leu  Gly  Gly  Pro  Ser  Gly  Ser  Ala  Ala  Leu  Lys  Ala  Ala  Val  Asp  Lys  Ala  Val  Ala
774     GAC  GTT  ATT  AAC  ATG  AGC  CTC  GGC  GGA  CCT  TCT  GGT  TCT  GCT  GCT  TTA  AAA  GCG  GCA  GTT  GAT  AAA  GCC  GTT  GCA

150                                                 Ser  Thr 160
        Ser  Gly  Val  Val  Val  Ala  Ala  Gly  Asn  Glu  Gly  Thr  Ser  Gly  Ser  Ser  Ser  Thr  Val  Gly  Tyr  Pro  Gly
849     TCC  GGT  GTC  GTA  GTT  GCG  GCA  GGT  AAC  GAA  GGC  ACT  TCC  AGC  TCA  AGC  ACA  GTG  GGC  TAC  CCT  GGT
```

FIG. 3B

```
              170                                      180                                   190
     Lys Tyr Pro Ser Val Ile Ala Val Gly Ala Val Asp Ser Ser Asn Gln Arp Ala Ser Phe Ser Val Gly Pro
 924 AAA TAC CCT TCT GTC ATT GCA GTA GGC GCT GTT GAC AGC AGC AAC CAA AGA GCA TCT TTC TCA AGC GTA GGA CCT 200                                      210
     Glu Leu Asp Val Met Ala Pro Gly Val Ser Ile Gln Ser Thr Leu Pro Gly Asn Lys Tyr Gly Ala Tyr Asn Gly
 999 GAG CTT GAT GTC ATG GCA CCT GGC GTA TCT ATC CAA AGC ACG CTT CCT GGA AAC AAA TAC GGG GCG TAC AAC GGT 220                                      230                                   240
     Thr Ser Met Ala Ser Pro His Val Ala Gly Ala Ala Leu Ile Leu Ser Lys His Pro Asn Trp Thr Asn Thr
1074 ACG TCA ATG GCA TCT CCG CAC GTT GCC GGA GCT GCT TTG ATT CTT TCT AAG CAC CCG AAC TGG ACA AAC ACT

250
     Gln Val Arg Ser Ser Leu Glu Asn Thr Thr Lys Leu Gly Asp Ser Phe Tyr Tyr Gly Lys Gly Leu Ile Asn
1149 CAA GTC CGC AGC AGT TTA GAA AAC ACC ACA AAA CTT GGT GAT TCT TTG TAC TAT GGA AAA GGG CTG ATC AAC 270                        275
     Val Gln Ala Ala Ala Gln Gln OC
1224 GTA CAA GCG GCA GCT CAG TAA     AACATAAAAACCGGGCCTTGGCCCCGGCCGGTTTTTATTATTTTCTTCCTCCGCATGTCAATCGGCTCC
                                                               TERM

1316 ATAATCGACGGATGGCTCCCTCTGAAAATTTTAACGAGAAACGGGGTTGACCGGCTCAGTCCGTAACGGCCAACTCCTGAAACGTCTCAATCGCCG

1416 CTTCCCGGTTTCCGGTCAGCTCAATGCCATAACGGTCGGGCGGTTTTCCTGATACGGGAGACGGGCATTCGTAATCGGATC
```

FIG. 3C

CONSERVED RESIDUES IN SUBTILISINS FROM
*BACILLUS AMYLOLIQUEFACIENS*

| | | |
|---|---|---|
| ATG AAG AAA CCG TTG GGG AAA ATT GTC GCA AGC ACC GCA CTA CTC ATT<br>Met Lys Lys Pro Leu Gly Lys Ile Val Ala Ser Thr Ala Leu Leu Ile<br>-111 -110                   -105                   -100 | 48 |
| TCT GTT GCT TTT AGT TCA TCG ATC GCA TCG GCT GCT GAA GAA GCA AAA<br>Ser Val Ala Phe Ser Ser Ser Ile Ala Ser Ala Ala Glu Glu Ala Lys<br>-95               -90               -85               -80 | 96 |
| GAA AAA TAT TTA ATT GGC TTT AAT GAG CAG GAA GCT GTC AGT GAG TTT<br>Glu Lys Tyr Leu Ile Gly Phe Asn Glu Gln Glu Ala Val Ser Glu Phe<br>               -75               -70               -65 | 144 |
| GTA GAA CAA GTA GAG GCA AAT GAC GAG GTC GCC ATT CTC TCT GAG GAA<br>Val Glu Gln Val Glu Ala Asn Asp Glu Val Ala Ile Leu Ser Glu Glu<br>        -60               -55               -50 | 192 |
| GAG GAA GTC GAA ATT GAA TTG CTT CAT GAA TTT GAA ACG ATT CCT GTT<br>Glu Glu Val Glu Ile Glu Leu Leu His Glu Phe Glu Thr Ile Pro Val<br>        -45               -40               -35 | 240 |
| TTA TCC GTT GAG TTA AGC CCA GAA GAT GTG GAC GCG CTT GAA CTC GAT<br>Leu Ser Val Glu Leu Ser Pro Glu Asp Val Asp Ala Leu Glu Leu Asp<br>    -30               -25               -20 | 288 |
| CCA GCG ATT TCT TAT ATT GAA GAG GAT GCA GAA GTA ACG ACA ATG GCG<br>Pro Ala Ile Ser Tyr Ile Glu Glu Asp Ala Glu Val Thr Thr Met Ala<br>-15               -10               -5                1 | 336 |
| CAA TCA GTG CCA TGG GGA ATT AGC CGT GTG CAA GCC CCA GCT GCC CAT<br>Gln Ser Val Pro Trp Gly Ile Ser Arg Val Gln Ala Pro Ala Ala His<br>          5                 10                15 | 384 |
| AAC CGT GGA TTG ACA GGT TCT GGT GTA AAA GTT GCT GTC CTC GAT ACA<br>Asn Arg Gly Leu Thr Gly Ser Gly Val Lys Val Ala Val Leu Asp Thr<br>       20               25                30 | 432 |
| GGT ATT TCC ACT CAT CCA GAC TTA AAT ATT CGT GGT GGC GCT AGC TTT<br>Gly Ile Ser Thr His Pro Asp Leu Asn Ile Arg Gly Gly Ala Ser Phe<br>       35               40                45 | 480 |
| GTA CCA GGG GAA CCA TCC ACT CAA GAT GGG AAT GGG CAT GGC ACG CAT<br>Val Pro Gly Glu Pro Ser Thr Gln Asp Gly Asn Gly His Gly Thr His<br>50                55                60                65 | 528 |
| GTG GCC GGG ACG ATT GCT GCT TTA GAC AAC TCG ATT GGC GTT CTT GGC<br>Val Ala Gly Thr Ile Ala Ala Leu Asp Asn Ser Ile Gly Val Leu Gly<br>               70                75                80 | 576 |
| GTA GCG CCG AGC GCG GAA CTA TAC GCT GTT AAA GTA TTA GGG GCG AGC<br>Val Ala Pro Ser Ala Glu Leu Tyr Ala Val Lys Val Leu Gly Ala Ser<br>           85                90                95 | 624 |
| GGT TCA GGC GCC ATC AGC TCG ATT GCC CAA GGA TTG GAA TGG GCA GGG<br>Gly Ser Gly Ala Ile Ser Ser Ile Ala Gln Gly Leu Glu Trp Ala Gly<br>          100              105              110 | 672 |

FIG. 5A

```
AAC AAT GGC ATG CAC GTT GCT AAT TTG AGT TTA GGA AGC CCT TCG CCA        720
Asn Asn Gly Met His Val Ala Asn Leu Ser Leu Gly Ser Pro Ser Pro
    115                 120                 125

AGT GCC ACA CTT GAG CAA GCT GTT AAT AGC GCG ACT TCT AGA GGC GTT        768
Ser Ala Thr Leu Glu Gln Ala Val Asn Ser Ala Thr Ser Arg Gly Val
130                 135                 140                 145

CTT GTT GTA GCG GCA TCT GGG AAT GAA GGT GCA GGC TCA ATC GAC TAT        816
Leu Val Val Ala Ala Ser Gly Asn Glu Gly Ala Gly Ser Ile Asp Tyr
                150                 155                 160

CCG GCC CGT TAT GCG AAC GCA ATG GCA GTC GGA GCT ACT GAC CAA AAC        864
Pro Ala Arg Tyr Ala Asn Ala Met Ala Val Gly Ala Thr Asp Gln Asn
            165                 170                 175

AAC AAC CGC GCC AGC TTT TCA CAG TAT GGC GCA GGG CTT GAC ATT GTC        912
Asn Asn Arg Ala Ser Phe Ser Gln Tyr Gly Ala Gly Leu Asp Ile Val
        180                 185                 190

GCA CCA GGT GTA AAC GTG CAG AGC ACA TAC CCA ATT TCA ACG TAT GCC        960
Ala Pro Gly Val Asn Val Gln Ser Thr Tyr Pro Ile Ser Thr Tyr Ala
    195                 200                 205

AGC TTA AAC GGT ACA TCG ATG GCT ACT CCT CAT GTT GCA GGT GCA GCA       1008
Ser Leu Asn Gly Thr Ser Met Ala Thr Pro His Val Ala Gly Ala Ala
210                 215                 220                 225

GCC CTT GTT AAA CAA AAG AAC CCA TCT TGG TCC AAT GTA CAA ATC CGC       1056
Ala Leu Val Lys Gln Lys Asn Pro Ser Trp Ser Asn Val Gln Ile Arg
                230                 235                 240

AAT CAT CTA AAG AAT ACG GCA ACG AGC TTA GGA AGC ACG AAC TTG TAT       1104
Asn His Leu Lys Asn Thr Ala Thr Ser Leu Gly Ser Thr Asn Leu Tyr
            245                 250                 255

GGA AGC GGA CTT GTC AAT GCA GAA GCG GCA ACA CGC                       1140
Gly Ser Gly Leu Val Asn Ala Glu Ala Ala Thr Arg
        260                 265
```

PROTEASE ENZYMES FOR TOUGH CLEANING AND/OR SPOT AND FILM REDUCTION AND COMPOSITIONS INCORPORATING SAME

This application is a 35 U.S.C. §371 application based upon International application Ser. No. PCT/IB98/00853, filed Jun. 2 1998, which claims priority to U.S. Provisional Application Ser. No. 60/048,550, filed Jun. 4, 1997.

FIELD OF THE INVENTION

The present invention relates to protease enzymes for tough cleaning and/or spot and film reduction in various compositions and methods for their use, more particularly to protease enzymes which are carbonyl hydrolase variants.

BACKGROUND OF THE INVENTION

Various types of enzymes have long been used in laundry detergents to assist in the removal of certain stains from fabrics. Each class of enzyme (amylase, protease, etc.) generally catalyzes a different chemical reaction. For example, protease enzymes are known for their ability to hydrolyze (break down a compound into two or more simpler compounds) other proteins. This ability has been taken advantage of through the incorporation of naturally occurring or engineered protease enzymes to laundry detergent compositions.

In recent years the use of enzymes has also been investigated for use in automatic dishwashing compositions. Unfortunately, many enzymes, especially protease enzymes, do not translate well into the wash environment. Specifically, thermal stability, pH stability, oxidative stability and substrate specificity need to be optimized to ensure satisfactory performance.

To optimize the characteristics of the protease enzyme, a change in the amino acid sequence is frequently employed. A change of amino acid sequence may alter the properties of the enzyme to varying degrees depending upon the location, nature, and/or magnitude of the change in the amino acid sequence. Several attempts have been made to alter the amino acid sequence of protease enzymes in an attempt to alter their properties, with the goal of increasing the efficacy of the protease for cleaning uses such as in the wash environment.

Additionally, consumers interest in automatic dishwashing compositions which deliver tough food cleaning is increasing. Baked on dairy products and eggs have long been difficult to remove via automatic dishwashing. In addition, spotting and filming of glassware is a common problem in autodishwashing. Moreover, consumers now desire less handwashing or pre-washing of dishes and more cleaning ability delivered via the automatic dishwasher. Accordingly, the need remains for compositions which can deliver tough cleaning and/or spot and film reduction cleaning without spot/film formation. More particularly, the need remains for automatic dishwashing compositions which can deliver tough food cleaning and reduced spot/film formation via protease enzymes designed to deliver such benefits.

BACKGROUND ART

The following documents contain information which may or may not be relevant to the present invention:

WO 95/10615 to Genencor International, Inc.; WO 89/06270 to Novo Nordisk A/S; Kirk-Othmer, Encyclopedia of Chemical Technology, 4th. Ed., Vol. 9, Wiley 1994, pages 567–620, titled "Enzyme Applications-Industrial", Nielsen et al and the references therein. WO 95/10591 and WO 95/10592 to the Procter & Gamble Company.

SUMMARY OF THE INVENTION

This need is met via the present invention whereby compositions having a protease enzyme capable of tough food cleaning and reduced spotting/filming is provided. The preferred protease enzyme is a carbonyl hydrolase variant having an amino acid sequence not found in nature. The protease is engineered to deliver tough cleaning and/or spot and film reduction and reduced spotting and filming by providing the protease with trypsin-like specificity. Thus, the protease is highly effective on dairy soils such as milk and cheese and on egg yolk soils and significantly reduces the spotting and filming such soils may cause in the automatic dishwashing process. The protease is derived by replacement of a plurality of amino acid residues of a precursor carbonyl hydrolase with different amino acids. Furthermore, the preferred protease is engineered to have a higher level of bleach stability. In addition, the enzymes of the present invention may provide improved soil removal in laundry applications as well.

According to a first embodiment of the present invention, a cleaning composition is provided. The cleaning composition comprises:

(a) an effective amount of a protease enzyme which is a carbonyl hydrolase variant having an amino acid sequence not found in nature, which is derived by replacement of a plurality of amino acid residues of a precursor carbonyl hydrolase with different amino acids, wherein said plurality of amino acid residues replaced in the precursor enzyme correspond to position +210 in combination with one or more of the following residues: +33, +62, +67, +76, +100, +101, +103, +104, +107, +128, +129, +130, +132, +135, +156, +158, +164, +166, +167, +170, +209, +215, +217, +218 and +222, where the numbered positions correspond to naturally-occurring subtilisin from *Bacillus amyloliquefaciens* or to equivalent amino acid residues in other carbonyl hydrolases or subtilisins (such as *Bacillus lentus* subtilisin); and (b) one or more cleaning adjunct materials compatible with the protease enzyme.

Most preferably, the protease is derived by replacement of a plurality of amino acid residues of a precursor carbonyl hydrolase with different amino acids, wherein the plurality of amino acid residues replaced in the precursor enzyme correspond to position +210 in combination with one or more of the following residues: +76, +103, +104, +156, +166, and +217, +222, and most preferably, the protease is derived from replacing amino acid residues at positions +210, +76, +103, +104, +156, and +166.

The present invention also relates to methods for cleaning items in need of cleaning by contacting the item with a protease enzyme which is a carbonyl hydrolase variant as described herein. The invention therefore encompasses a method for cleaning fabrics comprising contacting, preferably with agitation, the fabrics with an aqueous liquor containing the protease enzyme. The method can be carried out at temperatures below about 60° C. but, of course, is quite effective at laundry temperatures up to the boil. The present invention also relates to a method for cleaning dishes by contacting a dish in need of cleaning with a protease enzyme as described herein. The present invention methods also include methods for personal cleansing, the methods comprising contacting the part of the human or lower animal body in need of cleaning with a protease enzyme as described herein.

Accordingly, it is an object of the present invention to provide a cleaning composition having a protease enzyme capable of tough cleaning, and/or spot and film reduction particularly an automatic dishwashing composition having tough soil or food cleaning. It is further an object of the present invention to provide methods for fabric, dish and personal cleansing via the use of the protease enzymes of the present invention. These, and other, objects, features and advantages will be clear from the following detailed description, the attached drawings and the appended claims.

All percentages, ratios and proportions herein are on a weight basis unless otherwise indicated. All documents cited herein are hereby incorporated by reference.

BRIEF DESCRIPTION OF THE DRAWINGS

FIGS. 1A and 1B depict the DNA and amino acid sequence of subtilisin from *Bacillus lentus* (Seq. ID No. 6 and 7). The mature subtilisin protein is coded by the codons beginning at the codon GCG (334–336) corresponding to Ala.

FIGS. 2A and 2B depict the amino acid sequence of four subtilisins. The top line represents the amino acid sequence of subtilisin from *Bacillus amyloliquefaciens* subtilisin (also sometimes referred to as subtilisin BPN') (Seq. ID No. 2). The second line depicts the amino acid sequence of subtilisin from *Bacillus subtilis* (Seq. ID No. 3). The third line depicts the amino acid sequence of subtilisin from *B. licheniformis* (Seq. ID No. 4). The fourth line depicts the amino acid sequence of subtilisin from *Bacillus lentus* (also referred to as subtilisin 309 in PCT WO 89/06276) (Seq. ID No. 5). The symbol * denotes the absence of specific amino acid residues as compared to subtilisin BPN'.

FIGS. 3A–C depict the DNA and amino acid sequence for *Bacillus amyloliquefaciens* subtilisin and a partial restriction map of this gene (Seq. ID No. 1).

FIG. 4 depicts the conserved amino acid residues among subtilisins from *Bacillus amyloliquefaciens* (BPN') and *Bacillus lentus* (wild-type).

FIGS. 5A and 5B depict the DNA and amino acid sequence of a preferred embodiment of the invention (P210I/S156E/S166D/N76D/S103A/V104I) (Seq. ID No. 8 and 9). The DNA in this figure has been modified by the methods described to encode aspartate at positions 76 and 166, glutamate at position 156, alanine at position 103 and isoleucine at positions 210 and 104. The mature subtilisin variant protein is coded by the codons beginning at the codon GCG (334–336) corresponding to ala.

DETAILED DESCRIPTION OF THE PREFERRED EMBODIMENTS

Figure 3A:
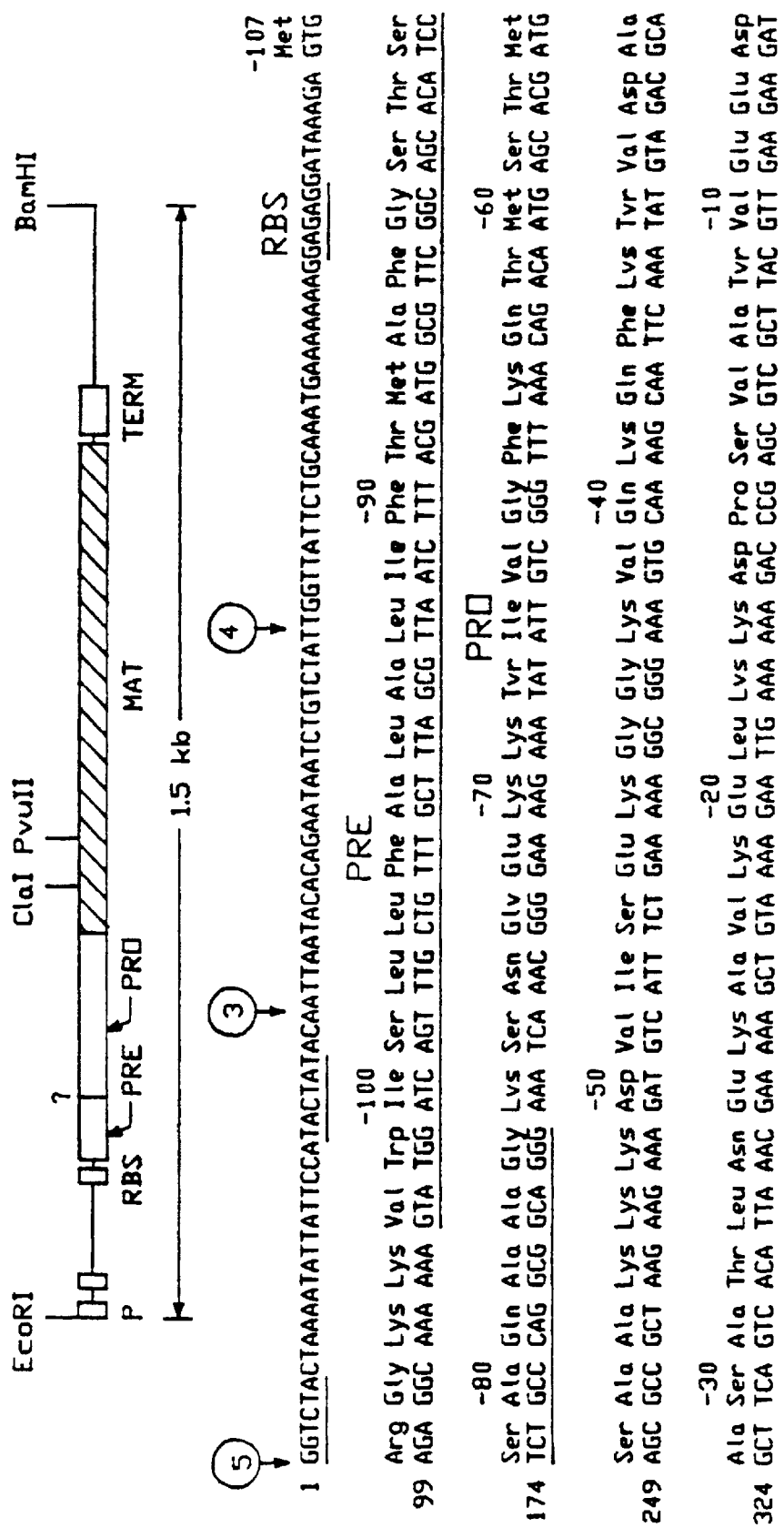

Protease Enzymes—The invention includes protease enzymes which are non-naturally-occurring carbonyl hydrolase variants having a different proteolytic activity, stability, substrate specificity, pH profile and/or performance characteristic as compared to the precursor carbonyl hydrolase from which the amino acid sequence of the variant is derived. As stated earlier, the protease enzymes are designed to have trypsin-like specificity and preferably also be bleach stable. The precursor carbonyl hydrolase may be a naturally-occurring carbonyl hydrolase or recombinant hydrolase. Specifically, such carbonyl hydrolase variants have an amino acid sequence not found in nature, which is derived by replacement of a plurality of amino acid residues of a precursor carbonyl hydrolase with different amino acids. The plurality of amino acid residues of the precursor enzyme correspond to position +210 in combination with one or more of the following residues: +33, +62, +67, +76, +100, +101, +103, +104, +107, +128, +129, +130, +132, +135, +156, +158, +164, +166, +167, +170, +209, +215, +217, +218, and +222, where the numbered position corresponds to naturally-occurring subtilisin from *Bacillus amyloliquefaciens* or to equivalent amino acid residues in other carbonyl hydrolases or subtilisins, such as *Bacillus lentus* subtilisin.

The carbonyl hydrolase variants which are protease enzymes useful in the present invention compositions comprise replacement of amino acid residue +210 in combination with one or more additional modifications. While any combination of the above listed amino acid substitutions may be employed, the preferred variant protease enzymes useful for the present invention comprise the substitution, deletion or insertion of amino acid residues in the following combinations: 210/156; 210/166; 210/76; 210/103; 210/104; 210/217; 210/156/166; 210/156/217; 210/166/217; 210/76/156; 210/76/166; 210/76/217; 210/76/156/166; 210/76/156/217; 210/76/166/217; 210/76/103/156; 210/76/103/166; 210/76/103/217; 210/76/104/156; 210/76/104/166; 210/76/104/217; 210/76/103/104/156; 210/76/103/104/166; 210/76/103/104/217; 210/76/103/104/156/166; 210/76/103/104/156/217; 210/76/103/104/166/217 and/or 210/76/103/104/156/166/217; 210/76/103/104/166/222; 210/67/76/103/104/166/222; 210/67/76/103/104/166/218/222. Most preferably the variant enzymes useful for the present invention comprise the substitution, deletion or insertion of an amino acid residue in the following combination of residues: 210/156; 210/166; 210/217; 210/156/166; 210/156/217; 210/166/217; 210/76/156/166; 210/76/103/156/166 and 210/76/103/104/156/166 of *B. lentus* subtilisin with 210/76/103/104/156/166 being the most preferred.

Variant DNA sequences encoding such carbonyl hydrolase or subtilisin variants are derived from a precursor DNA sequence which encodes a naturally-occurring or recombinant precursor enzyme. The variant DNA sequences are derived by modifying the precursor DNA sequence to encode the substitution of one or more specific amino acid residues encoded by the precursor DNA sequence corresponding to positions +210, +33, +62, +67, +76, +100, +101, +103, +104, +107, +128, +129, +130, +132, +135, +156, +158, +164, +166, +167, +170, +209, +215, +217, +218, and +222 in *Bacillus lentus* or any combination thereof. Although the amino acid residues identified for modification herein are identified according to the numbering applicable to *B. amyloliquefaciens* (which has become the conventional method for identifying residue positions in all subtilisins), the preferred precursor DNA sequence useful for the present invention is the DNA sequence of *Bacillus lentus* as shown in FIG. 1.

These variant DNA sequences encode the insertion or substitution of the amino acid residue +210 in combination with one or more additional modification. Preferably the variant DNA sequences encode the substitution or insertion of amino acid residues in the following combinations: 210/156; 210/166; 210/76; 210/103; 210/104; 210/217; 210/156/166; 210/156/217; 210/166/217; 210/76/156; 210/76/166; 210/76/217; 210/76/156/166; 210/76/156/217; 210/76/166/217; 210/76/103/156; 210/76/103/166; 210/76/103/217; 210/76/104/156; 210/76/104/166; 210/76/104/217; 210/76/103/104/156; 210/76/103/104/166; 210/76/103/104/217; 210/76/103/104/156/166; 210/76/103/104/156/217; 210/76/103/104/166/217 and/or 210/76/103/104/156/166/217; 210/76/103/104/166/222; 210/67/76/103/104/166/222; 210/67/76/103/104/166/218/222. Most preferably the variant DNA sequences encode for the modification of the following combinations of residues: 210/156; 210/166; 210/217; 210/156/166; 210/156/217; 210/166/217; 210/76/156/166; 210/76/103/156/166 and 210/76/103/104/156/166. These recombinant DNA sequences encode carbonyl hydrolase variants having a novel amino acid sequence and, in general, at least one property which is substantially different from the same property of the enzyme encoded by the precursor carbonyl hydrolase DNA sequence. Such properties include proteolytic activity, substrate specificity, stability, altered pH profile and/or enhanced performance characteristics.

The protease enzymes useful herein encompass the substitution of any of the nineteen naturally occurring L-amino acids at the designated amino acid residue positions. Such substitutions can be made in any precursor subtilisin (procaryotic, eucaryotic, mammalian, etc.). Throughout this application reference is made to various amino acids by way of common one- and three-letter codes. Such codes are identified in Dale, M. W. (1989), *Molecular Genetics of Bacteria,* John Wiley & Sons, Ltd., Appendix B.

Preferably, the substitution to be made at each of the identified amino acid residue positions include but are not limited to substitutions at position +210 including I, V, L, and A, substitutions at positions +33, +62, +76, +100, +101, +103, +104, +107, +128, +129, +130, +132, +135, +156, +158, +164, +166, +167, +170, +209, +215, +217, and +218 of D or E, substitutions at position 76 including D, H, E, G, F, K, P and N; substitutions at position 103 including Q, T, D, E, Y, K, G, R and S; and substitutions at position 104 including S, Y, I, L, M, A, W, D, T, G and V; and substitutions at position 222 including S, C, A. The specifically preferred amino acid(s) to be substituted at each such position are designated below in Table 1. Although specific amino acids are shown in Table I, it should be understood that any amino acid may be substituted at the identified residues.

TABLE I

| Amino Acid Residue | Preferred Amino Acid to be Substituted/Inserted |
| --- | --- |
| +210 | I, V, L, A |
| +33, +62, +100, +101, +107 +128, +129, +130, +135 +156, +158, +164, +166 +167, +170, +209, +215 +217 and +218 | D,E |
| +76 | D,H |
| +103 | A,Q,T,D,B,Y,K,G,R |
| +104 | I,Y,S,L,A,T,G |
| +222 | S,C,A |

Carbonyl hydrolases are protease enzymes which hydrolyze compounds containing

bonds in which X is oxygen or nitrogen. They include naturally-occurring carbonyl hydrolases and recombinant carbonyl hydrolases. Naturally-occurring carbonyl hydrolases principally include hydrolases, e.g., peptide hydrolases such as subtilisins or metalloproteases. Peptide hydrolases include α-aminoacylpeptide hydrolase, peptidylamino acid hydrolase, acylamino hydrolase, serine carboxypeptidase, metallocarboxypeptidase, thiol proteinase, carboxylproteinase and metalloproteinase. Serine, metallo, thiol and acid protease's are included, as well as endo and exo-proteases.

"Recombinant carbonyl hydrolase" refers to a carbonyl hydrolase in which the DNA sequence encoding the naturally-occurring carbonyl hydrolase is modified to produce a mutant DNA sequence which encodes the substitution, insertion or deletion of one or more amino acids in the carbonyl hydrolase amino acid sequence. Suitable modification methods are disclosed herein, and in U.S. Pat. Nos. 4,760,025, 5,204,015 and 5,185,258, the disclosure of which are incorporated herein by reference.

Figure 2B:
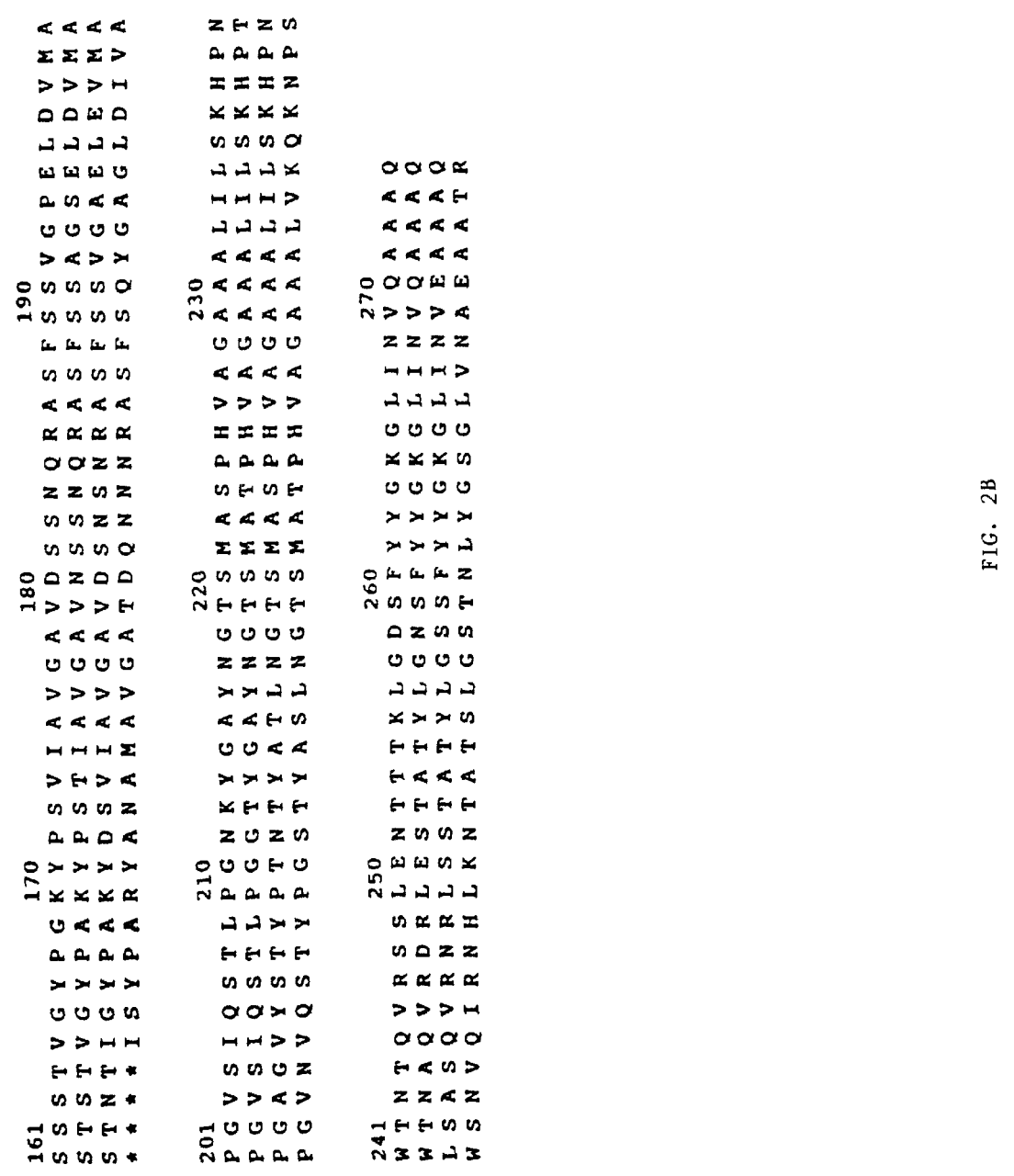

Subtilisins are bacterial or fungal carbonyl hydrolases which generally act to cleave peptide bonds of proteins or peptides. As used herein, "subtilisin" means a naturally-occurring subtilisin or a recombinant subtilisin. A series of naturally-occurring subtilisins is known to be produced and often secreted by various microbial species. Amino acid sequences of the members of this series are not entirely homologous. However, the subtilisins in this series exhibit the same or similar type of proteolytic activity. This class of serine proteases shares a common amino acid sequence defining a catalytic triad which distinguishes them from the chymotrypsin related class of serine proteases. The subtilisins and chymotrypsin related serine proteases both have a catalytic triad comprising aspartate, histidine and serine. In the subtilisin related proteases the relative order of these amino acids, reading from the amino to carboxy terminus, is aspartate-histidine-serine. In the chymotrypsin related proteases the relative order, however, is histidine-aspartate-serine. Thus, subtilisin herein refers to a serine protease having the catalytic triad of subtilisin related proteases. Examples include but are not limited to the subtilisins identified in FIG. 2 herein.

"Recombinant subtilisin" refers to a subtilisin in which the DNA sequence encoding the subtilisin is modified to produce a variant (or mutant) DNA sequence which encodes the substitution, deletion or insertion of one or more amino acids in the naturally-occurring subtilisin amino acid sequence. Suitable methods to produce such modification and which may be combined with those disclosed herein, include those disclosed in U.S. Pat. Nos. 4,760,025, 5,204, 015 and 5,185,258.

"Non-human carbonyl hydrolases" and the DNA encoding them may be obtained from many procaryotic and eucaryotic organisms. Suitable examples of procaryotic organisms include gram negative organisms such as *E. coli* or Pseudomonas and gram positive bacteria such as Micrococcus or Bacillus. Examples of eucaryotic organisms from which carbonyl hydrolase and their genes may be obtained include yeast such as *Saccharomyces cerevisiae,* fungi such as Aspergillus sp. and non-human mammalian sources such as, for example, *bovine* sp. from which the gene encoding the carbonyl hydrolase chymosin can be obtained. As with subtilisins, a series of carbonyl hydrolases can be obtained from various related species which have amino acid sequences which are not entirely homologous between the members of that series but which nevertheless exhibit the same or similar type of biological activity. Thus, non-human carbonyl hydrolase as used herein has a functional definition which refers to carbonyl hydrolases which are associated, directly or indirectly, with procaryotic and eucaryotic sources.

A "carbonyl hydrolase variant" has an amino acid sequence which is derived from the amino acid sequence of a "precursor carbonyl hydrolase." The precursor carbonyl hydrolases include naturally-occurring carbonyl hydrolases and recombinant carbonyl hydrolases. The amino acid sequence of the carbonyl hydrolase variant is "derived" from the precursor hydrolase amino acid sequence by the substitution, deletion or insertion of one or more amino acids of the precursor amino acid sequence. Such modification is of the "precursor DNA sequence" which encodes the amino acid sequence of the precursor carbonyl hydrolase rather than manipulation of the precursor carbonyl hydrolase enzyme per se. Suitable methods for such manipulation of the precursor DNA sequence include methods disclosed herein and in U.S. Pat. No. 4,760,025.

Specific residues corresponding to position +210 in combination with one or more of the following positions +33, +62, +67, +76, +100, +101, +103, +104, +107, +128, +129, +130, +132, +135, +156, +158, +164, +166, +167, +170, +209, +215, +217, +218 and +222 of *Bacillus lentus* subtilisin are identified herein for mutation. Preferably the modified residues are selected from the following combinations: 210/156; 210/166; 210/76; 210/103; 210/104; 210/217; 210/156/166; 210/156/217; 210/166/217; 210/76/156; 210/76/166; 210/76/217; 210/76/156/166; 210/76/156/217; 210/76/166/217; 210/76/103/156; 210/76/103/166; 210/76/103/217; 210/76/104/156; 210/76/104/166; 210/76/104/217; 210/76/103/104/156; 210/76/103/104/166; 210/76/103/104/217; 210/76/103/104/156/166; 210/76/103/104/156/217; 210/76/103/104/166/217 and/or 210/76/103/104/156/166/217 with preferred combinations being: 210/156; 210/166; 210/217; 210/156/166; 210/156/217; 210/166/217; 210/76/156/166; 210/76/103/156/166 and 210/76/103/104/156/166. These amino acid position numbers refer to those assigned to the mature *Bacillus amyloliquefaciens* subtilisin sequence presented in FIG. 3. The protease enzymes useful in the present invention, however, are not limited to the mutation of this particular subtilisin but extends to precursor carbonyl hydrolases containing amino acid residues at positions which are "equivalent" to the particular identified residues in *Bacillus amyloliquefaciens* subtilisin. Preferably, the precursor subtilisin is *Bacillus lentus* subtilisin and the substitutions, deletions or insertions are made at the equivalent amino acid residue in *B. lentus* corresponding to those listed above.

A residue (amino acid) of a precursor carbonyl hydrolase is equivalent to a residue of *Bacillus amyloliquefaciens* subtilisin if it is either homologous (i.e., corresponding in position in either primary or tertiary structure) or analogous to a specific residue or portion of that residue in *Bacillus amyloliquefaciens* subtilisin (i.e., having the same or similar functional capacity to combine, react, or interact chemically).

In order to establish homology to primary structure, the amino acid sequence of a precursor carbonyl hydrolase is directly compared to the *Bacillus amyloliquefaciens* subtilisin primary sequence and particularly to a set of residues known to be invariant in subtilisins for which sequence is known. FIG. 4 herein shows the conserved residues as between amyloliquefaciens subtilisin and *B. lentus* subtilisin. After aligning the conserved residues, allowing for necessary insertions and deletions in order to maintain alignment (i.e., avoiding the elimination of conserved residues through arbitrary deletion and insertion), the residues equivalent to particular amino acids in the primary sequence of *Bacillus amyloliquefaciens* subtilisin are defined. Alignment of conserved residues preferably should conserve 100% of such residues. However, alignment of greater than 75% or as little as 50% of conserved residues is also adequate to define equivalent residues. Conservation of the catalytic triad, Asp32/His64/Ser221 should be maintained.

For example, in FIG. 2 the amino acid sequence of subtilisin from *Bacillus amyloliquefaciens, Bacillus subtilis, Bacillus licheniformis* (carlsbergensis) and *Bacillus lentus* are aligned to provide the maximum amount of homology between amino acid sequences. A comparison of these sequences shows that there are a number of conserved residues contained in each sequence. These conserved residues (as between BPN' and *B. lentus*) are identified in FIG. 4.

These conserved residues, thus, may be used to define the corresponding equivalent amino acid residues of *Bacillus amyloliquefaciens* subtilisin in other carbonyl hydrolases such as subtilisin from *Bacillus lentus* (PCT Publication No. WO89/06279 published Jul. 13, 1989) and the preferred subtilisin precursor enzyme herein. These particular amino acid sequences are aligned in FIGS. 2A and 2B with the sequence of *Bacillus amyloliquefaciens* subtilisin to produce the maximum homology of conserved residues. As can be seen, there are a number of deletions in the sequence of *Bacillus lentus* as compared to *Bacillus amyloliquefaciens* subtilisin. Thus, for example, the equivalent amino acid for Val165 in *Bacillus amyloliquefaciens* subtilisin in the other subtilisins is isoleucine for *B. lentus* and *B. licheniformis*.

Thus, for example, the amino acid at position +210 is proline (P) in both *B. amyloliquefaciens* and *B. lentus* subtilisins. In the preferred subtilisin variant useful in the invention, however, the amino acid equivalent to +210 in *Bacillus amyloliquefaciens* subtilisin is substituted with isoleucine (I). A comparison of the preferred amino acid residues identified herein for substitution versus the preferred substitution for each such position is provided in Table II.

TABLE II

|  | +210 | +156 | +166 | +217 | +76 | +103 | +104 |
|---|---|---|---|---|---|---|---|
| B. amyloliquefaciens (wild-type) | P | E | G | Y | N | Q | Y |
| B. lentus (wild-type) | P | S | S | L | N | S | V |
| Most Preferred Substitution | I | E/D | E/D | E/D | D | A | I/Y |

Equivalent residues may also be defined by determining homology at the level of tertiary structure for a precursor carbonyl hydrolase whose tertiary structure has been determined by x-ray crystallography. Equivalent residues are defined as those for which the atomic coordinates of two or more of the main chain atoms of a particular amino acid residue of the precursor carbonyl hydrolase and *Bacillus amyloliquefaciens* subtilisin (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the carbonyl hydrolase in question to the *Bacillus amyloliquefaciens* subtilisin. The best model is the crystallographic model giving the lowest R factor for experimental diffraction data at the highest resolution available.

$$R\ factor = \frac{\Sigma_h |Fo(h)| - |Fc(h)|}{\Sigma_h |Fo(h)|}$$

Equivalent residues which are functionally analogous to a specific residue of *Bacillus amyloliquefaciens* subtilisin are defined as those amino acids of the precursor carbonyl hydrolases which may adopt a conformation such that they either alter, modify or contribute to protein structure, substrate binding or catalysis in a manner defined and attributed to a specific residue of the *Bacillus amyloliquefaciens* subtilisin. Further, they are those residues of the precursor carbonyl hydrolase (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *Bacillus amyloliquefaciens* subtilisin. The coordinates of the three dimensional structure of *Bacillus amyloliquefaciens* subtilisin are set forth in EPO Publication No. 0 251 446 (equivalent to U.S. patent application Ser. No. 07/898,382, the disclosure of which is incorporated herein by reference) and can be used as outlined above to determine equivalent residues on the level of tertiary structure.

Some of the residues identified for substitution, insertion or deletion are conserved residues whereas others are not. In the case of residues which are not conserved, the replacement of one or more amino acids is limited to substitutions which produce a variant which has an amino acid sequence that does not correspond to one found in nature. In the case of conserved residues, such replacements should not result in a naturally-occurring sequence. The carbonyl hydrolase variants useful in the present invention include the mature forms of carbonyl hydrolase variants, as well as the pro- and prepro-forms of such hydrolase variants. The prepro-forms are the preferred construction since this facilitates the expression, secretion and maturation of the carbonyl hydrolase variants.

Methods and procedures for making the enzymes according to the present invention are known and are disclosed in PCT Publication No. WO 95/10615 the disclosure of which is herein incorporated by reference.

The enzymes of the present invention have trypsin-like specificity. That is, the enzymes of the present invention hydrolyze proteins by preferentially cleaving the peptide bonds of charged amino acid residues, more specifically residues such as arginine and lysine, rather than preferentially cleaving the peptide bonds of hydrophobic amino acid residues, more specifically phenylalanine, tryptophan and tyrosine. Enzymes having the latter profile have a chymotrypsin-like specificity. Substrate specificity as discussed above is illustrated by the action of the enzyme on two synthetic substrates. Protease's having trypsin-like specificity hydrolyze the synthetic substrate bVGR-pNA preferentially over the synthetic substrate sucAAPF-pNA. Chymotrypsin-like protease enzymes, in contrast, hydrolyze the latter much faster than the former. For the purposes of the present invention the following procedure was employed to define the trypsin-like specificity of the protease enzymes of the present invention:

A fixed amount of a glycine buffer at a pH of 10 and a temperature of 25 ° C. is added to a standard 10 ml test tube. 0.5 ppm of the active enzyme to be tested is added to the test tube. Approximately, 1.25 mg of the synthetic substrate per mL of buffer solution is added to the test tube. The mixture is allowed to incubate for 15 minutes at 25° C. Upon completion of the incubation period, an enzyme inhibitor, PMSF, is added to the mixture at a level of 0.5 mg per mL of buffer solution. The absorbency or OD value of the mixture is read at a 410 nm wavelength. The absorbence then indicates the activity of the enzyme on the synthetic substrate. The greater the absorbence, the higher the level of activity against that substrate.

To then determine the specificity of an individual enzyme, the absorbence on the two synthetic substrate proteins may be converted into a specificity ratio. For the purposes of the present invention, the ratio is determined by the formula specificity of:

[activity on sAAPF-pNA]/[activity on bVGR-pNA]

An enzyme having a ratio of less than about 10, more preferably less than about 5 and most preferably less than about 2.5 may then be considered to demonstrate trypsin-like activity.

Cleaning Adjunct Materials—The cleaning compositions of the present invention also comprise, in addition to the protease enzyme described hereinbefore, one or more cleaning adjunct materials compatible with the protease enzyme. The term "cleaning adjunct materials", as used herein, means any liquid, solid or gaseous material selected for the particular type of cleaning composition desired and the form of the product (e.g., liquid; granule; spray composition), which materials are also compatible with the protease enzyme used in the composition. The specific selection of cleaning adjunct materials are readily made by considering the surface, item or fabric to be cleaned, and the desired form of the composition for the cleaning conditions during use (e.g., through the wash detergent use). The term "compatible", as used herein, means the cleaning composition materials do not reduce the proteolytic activity of the protease enzyme to such an extent that the protease is not effective as desired during normal use situations. Specific cleaning composition materials are exemplified in detail hereinafter.

An effective amount of one or more protease enzymes described above are included in compositions useful for cleaning a variety of surfaces in need of proteinaceous stain removal. Such cleaning compositions include detergent compositions for cleaning hard surfaces, unlimited in form (e.g., liquid and granular); detergent compositions for cleaning fabrics, unlimited in form (e.g., granular, liquid and bar formulations); dishwashing compositions (unlimited in form and including both granular and liquid automatic dishwashing); oral cleaning compositions, unlimited in form (e.g., dentifrice, toothpaste and mouthwash formulations); and denture cleaning compositions, unlimited in form (e.g., liquid, tablet). As used herein, "effective amount of protease enzyme" refers to the quantity of protease enzyme described hereinbefore necessary to achieve the enzymatic activity necessary in the specific cleaning composition. Such effective amounts are readily ascertained by one of ordinary skill in the art and is based on many factors, such as the particular enzyme variant used, the cleaning application, the specific composition of the cleaning composition, and whether a liquid or dry (e.g., granular, bar) composition is required, and the like.

Preferably the cleaning compositions of the present invention comprise from about 0.0001% to about 10% of one or more protease enzymes, more preferably from about 0.001% to about 1%, more preferably still from about 0.001% to about 0. 1%. Also preferably the protease enzyme is present in the compositions in an amount sufficient to provide a ratio of mg of active protease per 100 grams of composition to ppm theoretical Available $O_2$ ("Av$O_2$") from any peroxyacid in the wash liquor, referred to herein as the Enzyme to Bleach ratio (E/B ratio), ranging from about 1:1 to about 20:1. Several examples of various cleaning compositions wherein the protease enzymes may be employed are discussed in further detail below. Also, the compositions of the present invention may include from about 1% to about 99.9% by weight of the composition of the adjunct materials.

Optional Detersive Enzymes—The detergent compositions herein may also optionally contain one or more types of detergent enzymes. Such enzymes can include proteases, amylases, cellulases and lipases. Such materials are known in the art and are commercially available under such trademarks as. They may be incorporated into the non-aqueous liquid detergent compositions herein in the form of suspensions, "marumes" or "prills". Another suitable type of enzyme comprises those in the form of slurries of enzymes in nonionic surfactants, e.g., the enzymes marketed by Novo Nordisk under the tradename "SL" or the microencapsulated enzymes marketed by Novo Nordisk under the tradename "LDP." Suitable enzymes and levels of use are described in U.S. Pat. No. 5,576,282, 5,705,464 and 5,710,115.

Enzymes added to the compositions herein in the form of conventional enzyme prills are especially preferred for use herein. Such prills will generally range in size from about 100 to 1,000 microns, more preferably from about 200 to 800 microns and will be suspended throughout the non-aqueous liquid phase of the composition. Prills in the compositions of the present invention have been found, in comparison with other enzyme forms, to exhibit especially desirable enzyme stability in terms of retention of enzymatic activity over time. Thus, compositions which utilize enzyme prills need not contain conventional enzyme stabilizing such as must frequently be used when enzymes are incorporated into aqueous liquid detergents.

"Detersive enzyme", as used herein, means any enzyme having a cleaning, stain removing or otherwise beneficial effect in a laundry, hard surface cleaning or personal care detergent composition. Preferred detersive enzymes are hydrolases such as proteases, amylases and lipases. Preferred enzymes for laundry purposes include, but are not limited to, proteases, cellulases, lipases and peroxidases. Highly preferred for automatic dishwashing are amylases and/or proteases, including both current commercially available types and improved types which, though more and more bleach compatible though successive improvements, have a remaining degree of bleach deactivation susceptibility.

Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and known amylases, or mixtures thereof.

Examples of such suitable enzymes are disclosed in U.S. Pat. Nos. 5,705,464, 5,710,115, 5,576,282, 5,728,671 and 5,707,950

Particularly useful proteases are described in PCT publications: WO 95/30010 published Nov. 9, 1995 by The Procter & Gamble Company; WO 95/30011 published Nov. 9, 1995 by The Procter & Gamble Company; and WO 95/29979 published Nov. 9, 1995 by The Procter & Gamble Company. Suitable proteases are commercially available as ESPEPASE®, ALCALASE®, DURAZYM® and SAVINASE® all from Novo Nordisk A/S of Denmark, and as MAXATASE®, MAXACAL®, PROPERASE®, and MAXAPEM® all from Gist-Brocades of The Netherlands.

In addition to the peroxidase enzymes disclosed in U.S. Pat. Nos. 5,705,464, 5,710,115, 5,576,282, 5,728,671 and 5,707,950, other suitable peroxidase enzymes are disclosed in European Patent application EP No. 96870013.8, filed Feb. 20, 1996. Also suitable is the laccase enzyme.

Preferred enhancers are substituted phenthiazine and phenoxasine 10-Phenothiazinepropionicacid (PPT), 10-ethylphenothiazine-4-carboxylic acid (EPC), 10-phenoxazinepropionic acid (POP) and 10-methylphenoxazine (described in WO 94/12621) and substitued syringates (C3–C5 substitued alkyl syringates) and phenols. Sodium percarbonate or perborate are preferred sources of hydrogen peroxide.

Said peroxidases are normally incorporated in the detergent composition at levels from 0.0001% to 2% of active enzyme by weight of the detergent composition.

Other preferred enzymes that can be included in the detergent compositions of the present invention include lipases. Suitable lipase enzymes for detergent usage include those produced by microorganisms of the Pseudomonas group, such as Pseudomonas stutzeri ATCC 19.154, as disclosed in British Patent 1,372,034. Suitable lipases include those which show a positive immunological cross-reaction with the antibody of the lipase, produced by the microorganism *Pseudomonas fluorescent* IAM 1057. This lipase is available from Amano Pharmaceutical Co. Ltd., Nagoya, Japan, under the trade name Lipase P "Amano," hereinafter referred to as "Amano-P". Other suitable commercial lipases include Amano-CES, lipases ex *Chromobacter viscosum*, e.g. *Chromobacter viscosum var. lipolyticum* NRRLB 3673 from Toyo Jozo Co., Tagata, Japan; *Chromobacter viscosum* lipases from U.S. Biochemical Corp., U.S.A. and Disoynth Co., The Netherlands, and lipases ex *Pseudomonas gladioli*. Especially suitable lipases are lipases such as M1 LIPASE® and LIPOMAX®(Gist-Brocades) and LIPOLASE® and LIPOLASE ULTRA® (Novo) which have found to be very effective when used in combination with the compositions of the present invention.

Also suitable are cutinases [EC 3.1.1.50] which can be considered as a special kind of lipase, namely lipases which do not require interfacial activation. Addition of cutinases to detergent compositions have been described in e.g. WO 88/09367 (Genencor).

In addition to the above referenced lipases, phospholipases may be incorporated into the detergent compositions of the present invention. Nonlimiting examples of suitable phospholipases included: EC 3.1.1.32 Phospholipase A1; EC 3.1.1.4 Phospholipase A2; EC 3.1.1.5 Lysopholipase; EC 3.1.4.3 Phospholipase C; EC 3.1.4.4. Phospolipase D. Commercially available phospholipases include LECITASE® from Novo Nordisk A/S of Denmark and Phospholipase A2 from Sigma. When phospolipases are included in the compositions of the present invention, it is preferred that amylases are also included. Without desiring to be bound by theory, it is believed that the combined action of the phospholipase and amylase provide substantive stain removal, especially on greasy/oily, starchy and highly colored stains and soils. Preferably, the phospholipase and amylase, when present, are incorporated into the compositions of the present invention at a pure enzyme weight ratio between 4500:1 and 1:5, more preferably between 50:1 and 1:1.

Known amylases (α and/or β) can be included for removal of carbohydrate-based stains. WO 94/02597, Novo Nordisk A/S published Feb. 3, 1994, describes cleaning compositions which incorporate mutant amylases. See also WO94/18314, Genencor, published Aug. 18, 1994 and WO95/10603, Novo Nordisk A/S, published Apr. 20, 1995. Other amylases known for use in detergent compositions include both α- and β-amylases. α-Amylases are known in the art and include those disclosed in U.S. Pat. No. 5,003,257; EP 252,666; WO 91/00353; FR 2,676,456; EP 285,123; EP 525,610; EP 368,341; and British Patent Specification No. 1,296,839 (Novo). Other suitable amylase are stability-enhanced amylases including PURAFACT OX AM® described in WO 94/18314, published Aug. 18, 1994 and WO96/05295, Genencor, published Feb. 22, 1996 and amylase variants from Novo Nordisk A/S, disclosed in WO 95/10603, published April 1995.

Examples of commercial α-amylases products are TERMAMYL®, BAN®, FUNGAMYL® and DURAMYL®, all available from Novo Nordisk A/S Denmark. WO95/26397 describes other suitable amylases: α-amylases characterized by having a specific activity at least 25% higher than the specific activity of TERMAMYL® at a temperature range of 25° C. to 55° C. and at a pH value in the range of 8 to 10, measured by the Phadebas® α-amylase activity assay. Other amylolytic enzymes with improved properties with respect to the activity level and the combination of thermostability and a higher activity level are described in WO95/35382.

The above-mentioned enzymes may be of any suitable origin, such as vegetable, animal, bacterial, fungal and yeast origin. Purified or non-purified forms of these enzymes may be used. Also included by definition, are mutants of native enzymes. Mutants can be obtained e.g. by protein and/or genetic engineering, chemical and/or physical modifications of native enzymes. Common practice as well is the expression of the enzyme via host organisms in which the genetic material responsible for the production of the enzyme has been cloned.

Said enzymes are normally incorporated in the detergent composition at levels from 0.0001% to 2% of active enzyme by weight of the detergent composition. The enzymes can be added as separate single ingredients (prills, granulates, stabilized liquids, etc. containing one enzyme ) or as mixtures of two or more enzymes ( e.g. cogranulates).

Other suitable detergent ingredients that can be added are enzyme oxidation scavengers. Examples of such enzyme oxidation scavengers are ethoxylated tetraethylene polyamines.

A range of enzyme materials and means for their incorporation into synthetic detergent compositions is also disclosed in WO 9307263 and WO 9307260 to Genencor International, WO 8908694 to Novo, and U.S. Pat. No. 3,553,139, Jan. 5, 1971 to McCarty et al. Enzymes are further disclosed in U.S. Pat. No. 4,101,457, Place et al, Jul. 18, 1978, and in U.S. Pat. No. 4,507,219, Hughes, Mar. 26, 1985. Enzyme materials useful for liquid detergent formulations, and their incorporation into such formulations, are disclosed in U.S. Pat. No. 4,261,868, Hora et al, Apr. 14, 1981.

Enzyme Stabilizers—Enzymes for use in detergents can be stabilized by various techniques. Enzyme stabilization techniques are disclosed and exemplified in U.S. Pat. No. 3,600,319, Aug. 17, 1971, Gedge et al, EP 199,405 and EP 200,586, Oct. 29, 1986, Venegas. Enzyme stabilization systems are also described, for example, in U.S. Pat. No. 3,519,570. A useful Bacillus, sp. AC13 giving proteases, xylanases and cellulases, is described in WO 9401532 to Novo. The enzymes employed herein can be stabilized by the presence of water-soluble sources of calcium and/or magnesium ions in the finished compositions which provide such ions to the enzymes. Suitable enzyme stabilizers and levels of use are described in U.S. Pat. Nos. 5,705,464, 5,710,115 and 5,576,282.

Chelating Agents—The detergent compositions herein may also optionally contain a chelating agent which serves to chelate metal ions, e.g., iron and/or manganese, within the non-aqueous detergent compositions herein. Such chelating agents thus serve to form complexes with metal impurities in the composition which would otherwise tend to deactivate composition components such as the peroxygen bleaching agent. Useful chelating agents can include amino carboxylates, phosphonates, amino phosphonates, polyfunctionally-substituted aromatic chelating agents and mixtures thereof. Further examples of suitable chelating agents and levels of use are described in U.S. Pat. Nos. 5,705,464, 5,710,115 and 5,576,282.

Organic Builders—The compositions herein also optionally, but preferably, contain up to about 50%, more preferably from about 1% to about 40%, even more preferably from about 5% to about 30%, by weight of a detergent builder material. Lower or higher levels of builder, however, are not meant to be excluded. Detergent builders can optionally be included in the compositions herein to assist in controlling mineral hardness. Inorganic as well as organic builders can be used. Builders are typically used in fabric laundering compositions to assist in the removal of particulate soils. Suitable detergent builders are described in U.S. Pat. Nos. 5,705,464, 5,710,115, 5,576,282, 4,321,165 and 4,284,532. Preferred builders for use in liquid detergents herein are described in U.S. Pat. Nos. 5,705,464, 5,710,115, 5,576,282 and 4,284,532.

Inorganic Builders—The detergent compositions herein may also optionally contain one or more types of inorganic detergent builders beyond those listed hereinbefore that also finction as alkalinity sources. Such optional inorganic builders can include, for example, aluminosilicates such as zeolites. Aluminosilicate zeolites, and their use as detergent builders are more fully discussed in Corkill et al., U.S. Pat. No. 4,605,509; Issued Aug. 12, 1986, the disclosure of which is incorporated herein by reference. Also crystalline layered silicates, such as those discussed in this '509 U.S. patent, are also suitable for use in the detergent compositions herein. If utilized, optional inorganic detergent builders can comprise from about 2% to 15% by weight of the compositions herein. Additional examples of inorganic builders are described in U.S. Pat. Nos. 5,705,464 and 5,710,115.

Surfactants—Detersive surfactants included in the fully-formulated detergent compositions afforded by the present invention comprises at least 0.01%, preferably from about 0.5% to about 50%, by weight of detergent composition depending upon the particular surfactants used and the desired effects. In a highly preferred embodiment, the detersive surfactant comprises from about 0.5% to about 20% by weight of the composition.

The detersive surfactant can be nonionic, anionic, ampholytic, zwitterionic, or cationic nonlimiting examples of which are disclosed in U.S. Pat. Nos. 5,707,950 and 5,576,282. Mixtures of these surfactants can also be used. Preferred detergent compositions comprise anionic detersive surfactants or mixtures of anionic surfactants with other surfactants, especially nonionic surfactants.

Nonlimiting examples of surfactants useful herein include the conventional $C_{11}$–$C_{18}$ alkyl benzene sulfonates and primary, secondary and random alkyl sulfates, the $C_{10}$–$C_{18}$ alkyl alkoxy sulfates, the $C_{10}$–$C_{18}$ alkyl polyglycosides and their corresponding sulfated polyglycosides, $C_{12}$–$C_{18}$ alpha-sulfonated fatty acid esters, $C_{12}$–$C_{18}$ alkyl and alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like. Other conventional useful surfactants are listed in standard texts.

Particularly preferred surfactants in the preferred automatic dishwashing compositions (ADD) of the present invention are low foaming nonionic surfactants (LFNI) which are described in U.S. Pat. Nos. 5,705,464 and 5,710,115. LFNI may be present in amounts from 0.01% to about 10% by weight, preferably from about 0.1% to about 10%, and most preferably from about 0.25% to about 4%. LFNIs are most typically used in ADDs on account of the improved water-sheeting action (especially from glass) which they confer to the ADD product. They also encompass non-silicone, nonphosphate polymeric materials further illustrated hereinafter which are known to defoam food soils encountered in automatic dishwashing.

Preferred LFNIs include nonionic alkoxylated surfactants, especially ethoxylates derived from primary alcohols, and blends thereof with more sophisticated surfactants, such as the polyoxypropylene/polyoxyethylene/polyoxypropylene (PO/EO/PO) reverse block polymers as described in U.S. Pat. Nos. 5,705,464 and 5,710,115.

Highly preferred ADDs herein wherein the LFNI is present make use of ethoxylated monohydroxy alcohol or alkyl phenol and additionally comprise a polyoxyethylene, polyoxypropylene block polymeric compound as described in U.S. Pat. Nos. 5,705,464 and 5,710,115.

LFNIs which may also be used include those POLY-TERGENT® SLF-18 nonionic surfactants from Olin Corp., and any biodegradable LFNI having the melting point properties discussed hereinabove.

These and other nonionic surfactants are well known in the art, being described in more detail in Kirk Othmer's Encyclopedia of Chemical Technology, 3rd Ed., Vol. 22, pp. 360–379, "Surfactants and Detersive Systems", incorporated by reference herein.

Preferred are ADD compositions comprising mixed surfactants wherein the sudsing (absent any silicone suds controlling agent) is less than 2 inches, preferably less than 1 inch, as determined by the disclosure below.

The equipment useful for these measurements are: a Whirlpool Dishwasher (model 900) equipped with clear plexiglass door, IBM computer data collection with Labview and Excel Software, proximity sensor (Newark Corp.—model 95F5203) using SCXI interface, and a plastic ruler.

The data is collected as follows. The proximity sensor is affixed to the bottom dishwasher rack on a metal bracket. The sensor faces downward toward the rotating dishwasher arm on the bottom of the machine (distance approximately 2 cm. from the rotating arm). Each pass of the rotating arm is measured by the proximity sensor and recorded. The pulses recorded by the computer are converted to rotations per minute (RPM) of the bottom arm by counting pulses over a 30 second interval. The rate of the arm rotation is directly proportional to the amount of suds in the machine and in the dishwasher pump (i.e., the more suds produced, the slower the arm rotation).

The plastic ruler is clipped to the bottom rack of the dishwasher and extends to the floor of the machine. At the end of the wash cycle, the height of the suds is measured using the plastic ruler (viewed through the clear door) and recorded as suds height.

The following procedure is followed for evaluating ADD compositions for suds production as well as for evaluating nonionic surfactants for utility. (For separate evaluation of nonionic surfactant, a base ADD formula, such as Cascade powder, is used along with the nonionic surfactants which are added separately in glass vials to the dishwashing machine.)

First, the machine is filled with water (adjust water for appropriate temperature and hardness) and proceed through a rinse cycle. The RPM is monitored throughout the cycle (approximately 2 min.) without any ADD product (or surfactants) being added (a quality control check to ensure the machine is functioning properly). As the machine begins to fill for the wash cycle, the water is again adjusted for temperature and hardness, and then the ADD product is added to the bottom of the machine (in the case of separately evaluated surfactants, the ADD base formula is first added to the bottom of the machine then the surfactants are added by placing the surfactant-containing glass vials inverted on the top rack of the machine). The RPM is then monitored throughout the wash cycle. At the end of the wash cycle, the suds height is recorded using the plastic ruler. The machine is again filled with water (adjust water for appropriate temperature and hardness) and runs through another rinse cycle. The RPM is monitored throughout this cycle.

An average RPM is calculated for the 1st rinse, main wash, and final rinse. The % RPM efficiency is then calculated by dividing the average RPM for the test surfactants into the average RPM for the control system (base ADD formulation without the nonionic surfactant). The RPM efficiency and suds height measurements are used to dimension the overall suds profile of the surfactant.

Bleaching Agents—Hydrogen peroxide sources are described in detail in the herein incorporated Kirk Othmer's Encyclopedia of Chemical Technology, 4th Ed (1992, John Wiley & Sons), Vol. 4, pp. 271–300 "Bleaching Agents (Survey)", and include the various forms of sodium perborate and sodium percarbonate, including various coated and modified forms. An "effective amount" of a source of hydrogen peroxide is any amount capable of measurably improving stain removal (especially of tea stains) from soiled dishware compared to a hydrogen peroxide source-free composition when the soiled dishware is washed by the consumer in a domestic automatic dishwasher in the presence of alkali.

More generally a source of hydrogen peroxide herein is any convenient compound or mixture which under consumer use conditions provides an effective amount of hydrogen peroxide. Levels may vary widely and are usually in the range from about 0.1% to about 70%, more typically from about 0.5% to about 30%, by weight of the ADD compositions herein.

The preferred source of hydrogen peroxide used herein can be any convenient source, including hydrogen peroxide itself. For example, perborate, e.g., sodium perborate (any hydrate but preferably the mono- or tetra-hydrate), sodium carbonate peroxyhydrate or equivalent percarbonate salts, sodium pyrophosphate peroxyhydrate, urea peroxyhydrate, or sodium peroxide can be used herein. Also useful are sources of available oxygen such as persulfate bleach (e.g., OXONE, manufactured by DuPont). Sodium perborate monohydrate and sodium percarbonate are particularly preferred. Mixtures of any convenient hydrogen peroxide sources can also be used.

A preferred percarbonate bleach comprises dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Optionally, the percarbonate can be coated with a silicate, borate or water-soluble surfactants. Percarbonate is available from various commercial sources such as FMC, Solvay and Tokai Denka.

While not preferred for ADD compositions of the present invention which comprise detersive enzymes, the present invention compositions may also comprise as the bleaching agent a chlorine-type bleaching material. Such agents are well known in the art, and include for example sodium dichloroisocyanurate ("NaDCC").

While effective ADD compositions herein may comprise only the nonionic surfactant and builder, fully-formulated ADD compositions typically will also comprise other automatic dishwashing detergent adjunct materials to improve or modify performance. These materials are selected as appropriate for the properties required of an automatic dishwashing composition. For example, low spotting and filming is desired—preferred compositions have spotting and filming grades of 3 or less, preferably less than 2, and most preferably less than 1, as measured by the standard test of The American Society for Testing and Materials ("ASTM") D3556-85 (Reapproved 1989) "Standard Test Method for Deposition on Glassware During Mechanical Dishwashing".

(a) Bleach Activators—Preferably, the peroxygen bleach component in the composition is formulated with an activator (peracid precursor). The activator is present at levels of from about 0.01% to about 15%, preferably from about 0.5% to about 10%, more preferably from about 1% to about 8%, by weight of the composition. Preferred activators are selected from the group consisting of tetraacetyl ethylene diamine (TAED), benzoylcaprolactam (BzCL), 4-nitrobenzoylcaprolactam, 3-chlorobenzoylcaprolactam, benzoyloxybenzenesulphonate (BOBS), nonanoyloxybenzenesulphonate (NOBS), phenyl benzoate (PhBz), decanoyloxybenzenesulphonate ($C_{10}$-OBS), benzoylvalerolactam (BZVL), octanoyloxybenzenesulphonate ($C_8$-OBS), perhydrolyzable esters and mixtures thereof, most preferably benzoylcaprolactam and benzoylvalerolactam. Particularly preferred bleach activators in the pH range from about 8 to about 9.5 are those selected having an OBS or VL leaving group.

Preferred bleach activators are those described in U.S. Pat. Nos. 5,698,504, 5,695,679, 5,686,014, 5,130,045 and 4,412,934, and copending patent applications U.S. Ser. Nos. 08/064,624, 08/064,623, 08/064,621, 08/064,562, 08/064,564, 08/082,270 and copending application to M. Burns, A. D. Willey, R. T. Hartshorn, C. K. Ghosh, entitled "Bleaching Compounds Comprising Peroxyacid Activators Used With Enzymes" and having U.S. Ser. No. 08/133,691 (P&G Case 4890R), all of which are incorporated herein by reference.

The mole ratio of peroxygen bleaching compound (as AvO) to bleach activator in the present invention generally ranges from at least 1:1, preferably from about 20:1 to about 1:1, more preferably from about 10:1 to about 3:1.

Quaternary substituted bleach activators may also be included. The present detergent compositions preferably comprise a quaternary substituted bleach activator (QSBA) or a quaternary substituted peracid (QSP); more preferably, the former. Preferred QSBA structures are further described in copending U.S. Ser. No. 08/298,903, 08/298,650, 08/298,906 and 08/298,904 filed Aug. 31, 1994, now respectively U.S. Pat. Nos. 5,686,015, 5,460,747, 5,584,888 and 5,578,136, incorporated herein by reference.

Highly preferred bleach activators useful herein are amide-substituted as described in U.S. Pat. Nos. 5,698,504, 5,695,679 and 5,686,014. Preferred examples of such bleach activators include: (6-octanamidocaproyl) oxybenzenesulfonate, (6-nonanamidocaproyl) oxybenzenesulfonate, (6-decanamidocaproyl) oxybenzenesulfonate and mixtures thereof.

Other useful activators, disclosed in U.S. Pat. Nos. 5,698,504, 5,695,679, 5,686,014 and 4,966,723, include benzoxazin-type activators, such as a $C_6H_4$ ring to which is fused in the 1,2-positions a moiety —C(O)OC($R^1$)=N—.

Depending on the activator and precise application, good bleaching results can be obtained from bleaching systems having with in-use pH of from about 6 to about 13, preferably from about 9.0 to about 10.5. Typically, for example, activators with electron-withdrawing moieties are used for near-neutral or sub-neutral pH ranges. Alkalis and buffering agents can be used to secure such pH.

Acyl lactam activators, as described in U.S. Pat. Nos. 5,698,504, 5,695,679 and 5,686,014, are very useful herein, especially the acyl caprolactams (see for example WO 94-28102 A) and acyl valerolactams (see U.S. Pat. No. 5,503,639).

(b) Organic Peroxides, especially Diacyl Peroxides—These are extensively illustrated in Kirk Othmer, Encyclopedia of Chemical Technology, Vol. 17, John Wiley and Sons, 1982 at pages 27–90 and especially at pages 63–72, all incorporated herein by reference. If a diacyl peroxide is used, it will preferably be one which exerts minimal adverse impact on spotting/filming.

(c) Metal-containing Bleach Catalysts—The present invention compositions and methods utilize metal-containing bleach catalysts that are effective for use in ADD compositions. Preferred are manganese and cobalt-containing bleach catalysts.

One type of metal-containing bleach catalyst is a catalyst system comprising a transition metal cation of defined bleach catalytic activity, such as copper, iron, titanium, ruthenium tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. Nos. 5,576,282, 5,246,621, 5,244,594; 5,194,416; 5,114,606; and European Pat. App. Pub. Nos. 549,271A1, 549,272A1, 544,440A2, and 544,490A1; Preferred examples of these catalysts include $Mn^{IV}_2(u\text{-}O)_3(1,4,7\text{-trimethyl-1,4,7-triazacyclononane})_2(PF_6)_2$, $Mn^{III}_2(u\text{-}O)_1(u\text{-}OAc)_2(1,4,7\text{-trimethyl -1,4,7-triazacyclononane})_2(ClO_4)_2$, $Mn^{IV}_4(u\text{-}O)_6(1,4,7\text{-triazacyclononane})_4(ClO_4)_4$, $Mn^{III}Mn^{IV}_4(u\text{-}O)_1(u\text{-}OAc)_2\text{-}(1,4,7\text{-trimethyl-1,4,7-triazacyclononane})_2(ClO_4)_3$, $Mn^{IV}(1,4,7\text{-trimethyl-1,4,7-triazacyclononane})\text{-}(OCH_3)_3(PF_6)$, and mixtures thereof. Other metal-based bleach catalysts include those disclosed in U.S. Pat. Nos. 4,430,243 and 5,114,611. The use of manganese with various complex ligands to enhance bleaching is also reported in the following U.S. Pat. Nos: 4,728,455; 5,284,944; 5,246,612; 5,256,779; 5,280,117; 5,274,147; 5,153,161; and 5,227,084.

Cobalt bleach catalysts useful herein are known, and are described, for example, in U.S. Pat. Nos. 5,597,936, 5,595,967, 5,703,030 and M. L. Tobe, "Base Hydrolysis of Transition-Metal Complexes", Adv. Inorg. Bioinorg. Mech., (1983), 2, pages 1–94. The most preferred cobalt catalyst useful herein are cobalt pentaamine acetate salts having the formula $[Co(NH_3)_5OAc] T_y$, wherein "OAc" represents an acetate moiety and "$T_y$" is an anion, and especially cobalt pentaamine acetate chloride, $[Co(NH_3)_5OAc]Cl_2$; as well as $[Co(NH_3)_5OAc](OAc)_2$; $[Co(NH_3)_5OAc](PF_6)_2$; $[Co(NH_3)_5OAc](SO_4)$; $[Co(NH_3)_5OAc](BF_4)_2$; and $[Co(NH_3)_5OAc](NO_3)_2$ (herein "PAC").

These cobalt catalysts are readily prepared by known procedures, such as taught for example in U.S. Pat. Nos. 5,597,936, 5,595,967, 5,703,030, in the Tobe article and the references cited therein, and in U.S. Pat. No. 4,810,410, to Diakun et al, issued Mar. 7,1989, J. Chem. Ed. (1989), 66 (12), 1043–45; The Synthesis and Characterization of Inorganic Compounds, W. L. Jolly (Prentice-Hall; 1970), pp.

461–3; *Inorg. Chem.*, 18, 1497–1502 (1979); *Inorg. Chem.*, 21, 2881–2885 (1982); *Inorg. Chem.*, 18, 2023–2025 (1979); Inorg. Synthesis, 173–176 (1960); and *Journal of Physical Chemistry* 56, 22–25 (1952).

The bleach catalysts useful in automatic dishwashing compositions and concentrated powder detergent compositions may also be selected as appropriate for the present invention. For examples of suitable bleach catalysts see U.S. Pat. Nos. 4,246,612 and 5,227,084.

As a practical matter, and not by way of limitation, the compositions and cleaning processes herein can be adjusted to provide on the order of at least one part per hundred million of the active bleach catalyst species in the aqueous washing medium, and will preferably provide from about 0.01 ppm to about 25 ppm, more preferably from about 0.05 ppm to about 10 ppm, and most preferably from about 0.1 ppm to about 5 ppm, of the bleach catalyst species in the wash liquor. In order to obtain such levels in the wash liquor of an automatic washing process, typical compositions herein will comprise from about 0.0005% to about 0.2%, more preferably from about 0.004% to about 0.08%, of bleach catalyst, especially manganese or cobalt catalysts, by weight of the cleaning compositions.

pH and Buffering Variation—Many detergent compositions herein will be buffered, i.e., they are relatively resistant to pH drop in the presence of acidic soils. However, other compositions herein may have exceptionally low buffering capacity, or may be substantially unbuffered. Techniques for controlling or varying pH at recommended usage levels more generally include the use of not only buffers, but also additional alkalis, acids, pH-jump systems, dual compartment containers, etc., and are well known to those skilled in the art.

The preferred ADD compositions herein comprise a pH-adjusting component selected from water-soluble alkaline inorganic salts and water-soluble organic or inorganic builders as described in U.S. Pat. Nos. 5,705,464 and 5,710,115.

Water-Soluble Silicates—The present automatic dishwashing detergent compositions may further comprise water-soluble silicates as described in U.S. Pat. Nos. 5,705,464 and 5,710,115.

Material Care Agents—The preferred ADD compositions may contain one or more material care agents which are effective as corrosion inhibitors and/or anti-tarnish aids as described in U.S. Pat. Nos. 5,705,464, 5,710,115 and 5,646,101. When present, such protecting materials are preferably incorporated at low levels, e.g., from about 0.01% to about 5% of the ADD composition.

Other Materials—Detersive ingredients or adjuncts optionally included in the instant compositions can include one or more materials for assisting or enhancing cleaning performance, treatment of the substrate to be cleaned, or designed to improve the aesthetics of the compositions. Adjuncts which can also be included in compositions of the present invention, at their conventional art-established levels for use (generally, adjunct materials comprise, in total, from about 30% to about 99.9%, preferably from about 70% to about 95%, by weight of the compositions), include other active ingredients such as non-phosphate builders, chelants, enzymes, suds suppressors, dispersant polymers (e.g., from BASF Corp. or Rohm & Haas), color speckles, silvercare, anti-tarnish and/or anti-corrosion agents, dyes, fillers, germicides, alkalinity sources, hydrotropes, anti-oxidants, enzyme stabilizing agents, perfumes, solubilizing agents, carriers, processing aids, pigments, and pH control agents as described in U.S. Pat. Nos. 5,705,464, 5,710,115, 5,698,504, 5,695,679, 5,686,014 and 5,646,101.

The following nonlimiting examples further illustrate the ADD compositions of the present invention.

EXAMPLE 1

|  | Weight | |
| --- | --- | --- |
| Ingredients | A | B |
| Sodium Tripolyphosphate (STPP) | 24.0 | 45 |
| Sodium carbonate | 20.0 | 13.5 |
| Hydrated 2.0 r silicate | 15 | 13.5 |
| nonionic surfactants | 2.0 | 2.0 |
| Polymer[1] | 4.0 | — |
| Protease[2] (4% active) | 0.83 | 0.83 |
| Amylase (0.8% active) | 0.5 | 0.5 |
| Perborate monohydrate (15.5% Active AvO)[3] | 14.5 | 14.5 |
| Cobalt catalyst[4] | 0.008 | — |
| Dibenzoyl Peroxide (18% active) | 4.4 | 4.4 |
| Water, sodium sulfate and misc. | Balance | Balance |

[1]Terpolymer selected from either 60% acrylic acid/20% maleic acid/20% ethyl acrylate, or 70% acrylic acid/10% maleic acid/20% ethyl acrylate.
[2]A carbonyl hydrolase variant of B. amyloliquefaciens subtilisin with the amino acid substitutions 210I/76D/103A/104I/156E/166D.
[3]Available from DeGussa Corp. The AvO level of the above formula is 2.2%.
[4]Pentaammineacetatocobalt(III) nitrate prepared as described hereinbefore; may be replaced by MnTACN.

The ADD's of the above dishwashing detergent composition examples are used to wash milk-soiled glasses, starch, cheese, egg or babyfood- soiled flatware, by loading the soiled dishes in a domestic automatic dishwashing appliance and washing using either cold fill, 60° C. peak, or uniformly 45–50° C. wash cycles with a product concentration of the exemplary compositions of from about 1,000 to about 8,000 ppm, with excellent results.

EXAMPLE 2

Light-duty liquid dishwashing detergent formulae are prepared as follows:

|  | Composition | | |
| --- | --- | --- | --- |
|  | A | B | C |
| Ingredient | % Weight | | |
| Surfactant | 32.00 | 29.50 | 30.75 |
| Ethanol | 4.00 | 4.00 | 4.00 |
| Ammonium citrate | 0.06 | 0.06 | 0.06 |
| Magnesium chloride | 3.32 | 3.32 | 3.32 |
| Ammonium sulfate | 0.08 | 0.08 | 0.08 |
| Hydrogen peroxide | 200 ppm | 200 ppm | 200 ppm |
| Perfume | 0.18 | 0.18 | 0.18 |
| Protease[1] | 0.50 | 0.50 | 0.50 |
| Water and minors |  | Balance |  |

[1]A carbonyl hydrolase variant of B. amyloliquefaciens subtilisin with the amino acid substitutions 210I/76D/103A/104I/156E/166D.

Having described the invention in detail with reference to preferred embodiments and the examples, it will be clear to those skilled in the art that various changes and modifications may be made without departing from the scope of the invention and the invention is not to be considered limited to what is described in the specification.

What is claimed is:

1. A cleaning composition comprising:

(a) from about 0.1% to about 10% by weight of protease enzyme which is a carbonyl hydrolase variant having an amino acid sequence not found in nature, which is derived from a precursor carbonyl hydrolase consisting of a substitution of a different amino acid for a plurality of amino acid residues at a position in said precursor carbonyl hydrolase equivalent to position +210 in *Bacillus amyloliquefaciens* subtilisin, in combination with one or more amino acid residue positions equivalent to those selected from the group consisting of +33, +62, +67, +76, +100, +101, +103, +104, +107, +128, +129, +130, +132, +135, +156, +158, +164, +166, +167, +170, +209, +215, +217, +218, and +222 in *Bacillus amyloliquefaciens* subtilisin, provided that: when said carbonyl hydrolase variant includes a substitution at positions equivalent to +210 and +76, there is also a substitution of an amino acid residue at one or more of said amino acid residue positions other than amino acid residue positions equivalent to positions +101, +103, +104, +107, +128, +135, +156, +166, +217, +218 and +222; and (b) one or more cleaning adjunct materials compatible with the protease enzyme.

2. A cleaning composition according to claim 1 of wherein said cleaning composition is a dishwashing detergent composition comprising:

(a) from about 5% to about 90% by weight of the composition of a builder;

(b) from about 0.1% to about 15% by weight of the composition of detersive surfactant;

(c) optionally, from about 0.1% to about 40% by weight of the composition of a bleaching agent; and (d) cleaning adjunct materials.

3. The compositions according to claim 1 wherein the cleaning adjunct materials are selected from the group consisting of surfactants, solvents, buffers, enzymes, soil release agents, clay soil removal agents, dispersing agents, brighteners, suds suppressors, fabric softeners, suds boosters, enzyme stabilizers, builders, bleaching agents, dyes, perfumes, and mixtures thereof.

4. The composition according to claim 3 further comprising from about 5% to about 50% of a builder selected from the group consisting of zeolites, polycarboxylates, layered silicates, phosphates, and mixtures thereof.

5. The compositions according to claim 4 wherein the cleaning adjunct materials comprise at least one bleaching agent.

6. The compositions according to claim 5 wherein the bleaching agent is selected from the group consisting of percarbonates, perborates, and mixtures thereof, and optionally further comprising at least one bleach activator.

7. The compositions according to claim 6 wherein the composition further includes at least one detersive enzyme selected from the group consisting of cellulases, lipases, amylases, phospholipases, proteases, peroxidases and mixtures thereof.

8. A method for cleaning fabric, said method comprising contacting a fabric in need of cleaning with the composition as claimed in claim 1.

9. A method for cleaning dishes, said method comprising contacting a dish in need of cleaning with a composition according to claim 1.

10. A method for personal cleansing, said method comprising contacting the part of the human or lower animal body in need of cleaning with a composition according to claim 1.

11. A method for providing improved spotting and filming benefits in automatic dishwashing comprising contacting a dish in need of cleaning with a composition according to claim 1.

* * * * *

UNITED STATES PATENT AND TRADEMARK OFFICE
CERTIFICATE OF CORRECTION

PATENT NO.    : 6,369,011 B1
DATED         : April 9, 2002
INVENTOR(S)   : Saroj Rai et al.

It is certified that error appears in the above-identified patent and that said Letters Patent is hereby corrected as shown below:

<u>Title page,</u>
Item [57], ABSTRACT,
Line 2, should read -- ….which is a carbonyl hydrolase variant…. --.
Line 5, should read -- precursor carbonyl hydrolase…. --.

Signed and Sealed this

Third Day of September, 2002

*Attest:*

*Attesting Officer*

JAMES E. ROGAN
*Director of the United States Patent and Trademark Office*

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
       (A) LENGTH: 1497 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

```
GGTCTACTAA AATATTATTC CATACTATAC AATTAATACA CAGAATAATC TGTCTATTGG      60
TTATTCTGCA AATGAAAAAA AGGAGAGGAT AAAGAGTGAG AGGCAAAAAA GTATGGATCA     120
GTTTGCTGTT TGCTTTAGCG TTAATCTTTA CGATGGCGTT CGGCAGCACA TCCTCTGCCC     180
AGGCGGCAGG GAAATCAAAC GGGGAAAAGA AATATATTGT CGGGTTTAAA CAGACAATGA     240
GCACGATGAG CGCCGCTAAG AAGAAAGATG TCATTTCTGA AAAAGGCGGG AAAGTGCAAA     300
AGCAATTCAA ATATGTAGAC GCAGCTTCAG TCACATTAAA CGAAAAAGCT GTAAAAGAAT     360
TGAAAAAAGA CCCGAGCGTC GCTTACGTTG AAGAAGATCA CGTAGCACAT GCGTACGCGC     420
AGTCCGTGCC TTACGGCGTA TCACAAATTA AAGCCCCTGC TCTGCACTCT CAAGGCTACA     480
CTGGATCAAA TGTTAAAGTA GCGGTTATCG ACAGCGGTAT CGATTCTTCT CATCCTGATT     540
TAAAGGTAGC AAGCGGAGCC AGCATGGTTC CTTCTGAAAC AAATCCTTTC CAAGACAACA     600
ACTCTCACGG AACTCACGTT GCCGGCACAG TTGCGGCTCT TAATAACTCA ATCGGTGTAT     660
TAGGCGTTGC GCCAAGCGCA TCACTTTACG CTGTAAAAGT TCTCGGTGCT GACGGTTCCG     720
GCCAATACAG CTGGATCATT AACGGAATCG AGTGGGCGAT CGCAAACAAT ATGGACGTTA     780
TTAACATGAG CCTCGGCGGA CCTTCTGGTT CTGCTGCTTT AAAAGCGGCA GTTGATAAAG     840
CCGTTGCATC CGGCGTCGTA GTCGTTGCGG CAGCCGGTAA CGAAGGCACT TCCGGCAGCT     900
CAAGCACAGT GGGCTACCCT GGTAAATACC CTTCTGTCAT TGCAGTAGGC GCTGTTGACA     960
GCAGCAACCA AAGAGCATCT TTCTCAAGCG TAGGACCTGA GCTTGATGTC ATGGCACCTG    1020
GCGTATCTAT CCAAAGCACG CTTCCTGGAA ACAAATACGG GGCGTACAAC GGTACGTCAA    1080
TGGCATCTCC GCACGTTGCC GGAGCGGCTG CTTTGATTCT TTCTAAGCAC CCGAACTGGA    1140
CAAACACTCA AGTCCGCAGC AGTTTAGAAA ACACCACTAC AAAACTTGGT GATTCTTTGT    1200
ACTATGGAAA AGGGCTGATC AACGTACAAG CGGCAGCTCA GTAAAACATA AAAAACCGGC    1260
CTTGGCCCCG CCGGTTTTTT ATTATTTTTC TTCCTCCGCA TGTTCAATCC GCTCCATAAT    1320
CGACGGATGG CTCCCTCTGA AAATTTTAAC GAGAAACGGC GGGTTGACCC GGCTCAGTCC    1380
CGTAACGGCC AACTCCTGAA ACGTCTCAAT CGCCGCTTCC CGGTTTCCGG TCAGCTCAAT    1440
GCCATAACGG TCGGCGGCGT TTTCCTGATA CCGGGAGACG GCATTCGTAA TCGGATC       1497
```

(2) INFORMATION FOR SEQ ID NO:2:

(i) SEQUENCE CHARACTERISTICS:
       (A) LENGTH: 275 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:2:

```
Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ala Gly Gly Ala
            35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65              70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
130                 135                 140

Ser Gly Val Val Val Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
    275
```

(2) INFORMATION FOR SEQ ID NO:3:

(i) SEQUENCE CHARACTERISTICS:
        (A) LENGTH: 275 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Asn Val Arg Gly Gly Ala
            35                  40                  45
```

```
Ser Phe Val Pro Ser Glu Thr Asn Pro Tyr Gln Asp Gly Ser Ser His
    50                  55                  60
Gly Thr His Val Ala Gly Thr Ile Ala Ala Leu Asn Asn Ser Ile Gly
 65                  70                  75                  80
Val Leu Gly Val Ser Pro Ser Ala Ser Leu Tyr Ala Val Lys Val Leu
                 85                  90                  95
Asp Ser Thr Gly Ser Gly Gln Tyr Ser Trp Ile Ile Asn Gly Ile Glu
                100                 105                 110
Trp Ala Ile Ser Asn Asn Met Asp Val Ile Asn Met Ser Leu Gly Gly
            115                 120                 125
Pro Thr Gly Ser Thr Ala Leu Lys Thr Val Val Asp Lys Ala Val Ser
    130                 135                 140
Ser Gly Ile Val Val Ala Ala Ala Gly Asn Glu Gly Ser Ser Gly
145                 150                 155                 160
Ser Thr Ser Thr Val Gly Tyr Pro Ala Lys Tyr Pro Ser Thr Ile Ala
                165                 170                 175
Val Gly Ala Val Asn Ser Ser Asn Gln Arg Ala Ser Phe Ser Ser Ala
                180                 185                 190
Gly Ser Glu Leu Asp Val Met Ala Pro Gly Val Ser Ile Gln Ser Thr
            195                 200                 205
Leu Pro Gly Gly Thr Tyr Gly Ala Tyr Asn Gly Thr Ser Met Ala Thr
    210                 215                 220
Pro His Val Ala Gly Ala Ala Leu Ile Leu Ser Lys His Pro Thr
225                 230                 235                 240
Trp Thr Asn Ala Gln Val Arg Asp Arg Leu Glu Ser Thr Ala Thr Tyr
                245                 250                 255
Leu Gly Asn Ser Phe Tyr Tyr Gly Lys Gly Leu Ile Asn Val Gln Ala
                260                 265                 270
Ala Ala Gln
    275

(2) INFORMATION FOR SEQ ID NO:4:

(i) SEQUENCE CHARACTERISTICS:
        (A) LENGTH: 274 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Ala Gln Thr Val Pro Tyr Gly Ile Pro Leu Ile Lys Ala Asp Lys Val
 1                5                  10                  15
Gln Ala Gln Gly Phe Lys Gly Ala Asn Val Lys Val Ala Val Leu Asp
                 20                  25                  30
Thr Gly Ile Gln Ala Ser His Pro Asp Leu Asn Val Val Gly Gly Ala
            35                  40                  45
Ser Phe Val Ala Gly Glu Ala Tyr Asn Thr Asp Gly Asn Gly His Gly
    50                  55                  60
Thr His Val Ala Gly Thr Val Ala Ala Leu Asp Asn Thr Thr Gly Val
 65                  70                  75                  80
Leu Gly Val Ala Pro Ser Val Ser Leu Tyr Ala Val Lys Val Leu Asn
                 85                  90                  95
Ser Ser Gly Ser Gly Ser Tyr Ser Gly Ile Val Ser Gly Ile Glu Trp
                100                 105                 110
```

```
Ala Thr Thr Asn Gly Met Asp Val Ile Asn Met Ser Leu Gly Gly Ala
            115                 120                 125

Ser Gly Ser Thr Ala Met Lys Gln Ala Val Asp Asn Ala Tyr Ala Arg
        130                 135                 140

Gly Val Val Val Ala Ala Gly Asn Ser Gly Asn Ser Gly Ser
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Leu Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln (2) INFORMATION FOR SEQ ID NO:5:

(i) SEQUENCE CHARACTERISTICS:
        (A) LENGTH: 269 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175
```

```
Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                    245                 250                 255

Tyr Gly Ser Gly Leu Val Asn Ala Glu Ala Ala Thr Arg
            260                 265

(2) INFORMATION FOR SEQ ID NO:6:

(i) SEQUENCE CHARACTERISTICS:
        (A) LENGTH: 1140 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1140

(xi) SEQUENCE DESCRIPTION: SEQ ID NO:6:

ATG AAG AAA CCG TTG GGG AAA ATT GTC GCA AGC ACC GCA CTA CTC ATT       48
Met Lys Lys Pro Leu Gly Lys Ile Val Ala Ser Thr Ala Leu Leu Ile
  1               5                  10                  15

TCT GTT GCT TTT AGT TCA TCG ATC GCA TCG GCT GCT GAA GAA GCA AAA       96
Ser Val Ala Phe Ser Ser Ser Ile Ala Ser Ala Ala Glu Glu Ala Lys
                 20                  25                  30

GAA AAA TAT TTA ATT GGC TTT AAT GAG CAG GAA GCT GTC AGT GAG TTT      144
Glu Lys Tyr Leu Ile Gly Phe Asn Glu Gln Glu Ala Val Ser Glu Phe
             35                  40                  45

GTA GAA CAA GTA GAG GCA AAT GAC GAG GTC GCC ATT CTC TCT GAG GAA      192
Val Glu Gln Val Glu Ala Asn Asp Glu Val Ala Ile Leu Ser Glu Glu
         50                  55                  60

GAG GAA GTC GAA ATT GAA TTG CTT CAT GAA TTT GAA ACG ATT CCT GTT      240
Glu Glu Val Glu Ile Glu Leu Leu His Glu Phe Glu Thr Ile Pro Val
 65                  70                  75                  80

TTA TCC GTT GAG TTA AGC CCA GAA GAT GTG GAC GCG CTT GAA CTC GAT      288
Leu Ser Val Glu Leu Ser Pro Glu Asp Val Asp Ala Leu Glu Leu Asp
                 85                  90                  95

CCA GCG ATT TCT TAT ATT GAA GAG GAT GCA GAA GTA ACG ACA ATG GCG      336
Pro Ala Ile Ser Tyr Ile Glu Glu Asp Ala Glu Val Thr Thr Met Ala
            100                 105                 110

CAA TCA GTG CCA TGG GGA ATT AGC CGT GTG CAA GCC CCA GCT GCC CAT      384
Gln Ser Val Pro Trp Gly Ile Ser Arg Val Gln Ala Pro Ala Ala His
            115                 120                 125

AAC CGT GGA TTG ACA GGT TCT GGT GTA AAA GTT GCT GTC CTC GAT ACA      432
Asn Arg Gly Leu Thr Gly Ser Gly Val Lys Val Ala Val Leu Asp Thr
130                 135                 140

GGT ATT TCC ACT CAT CCA GAC TTA AAT ATT CGT GGT GGC GCT AGC TTT      480
Gly Ile Ser Thr His Pro Asp Leu Asn Ile Arg Gly Gly Ala Ser Phe
145                 150                 155                 160

GTA CCA GGG GAA CCA TCC ACT CAA GAT GGG AAT GGG CAT GGC ACG CAT      528
Val Pro Gly Glu Pro Ser Thr Gln Asp Gly Asn Gly His Gly Thr His
                165                 170                 175
```

```
GTG GCC GGG ACG ATT GCT GCT TTA AAC AAT TCG ATT GGC GTT CTT GGC      576
Val Ala Gly Thr Ile Ala Ala Leu Asn Asn Ser Ile Gly Val Leu Gly
            180                 185                 190

GTA GCG CCG AGC GCG GAA CTA TAC GCT GTT AAA GTA TTA GGG GCG AGC      624
Val Ala Pro Ser Ala Glu Leu Tyr Ala Val Lys Val Leu Gly Ala Ser
        195                 200                 205

GGT TCA GGT TCG GTC AGC TCG ATT GCC CAA GGA TTG GAA TGG GCA GGG      672
Gly Ser Gly Ser Val Ser Ser Ile Ala Gln Gly Leu Glu Trp Ala Gly
    210                 215                 220

AAC AAT GGC ATG CAC GTT GCT AAT TTG AGT TTA GGA AGC CCT TCG CCA      720
Asn Asn Gly Met His Val Ala Asn Leu Ser Leu Gly Ser Pro Ser Pro
225                 230                 235                 240

AGT GCC ACA CTT GAG CAA GCT GTT AAT AGC GCG ACT TCT AGA GGC GTT      768
Ser Ala Thr Leu Glu Gln Ala Val Asn Ser Ala Thr Ser Arg Gly Val
            245                 250                 255

CTT GTT GTA GCG GCA TCT GGG AAT TCA GGT GCA GGC TCA ATC AGC TAT      816
Leu Val Val Ala Ala Ser Gly Asn Ser Gly Ala Gly Ser Ile Ser Tyr
        260                 265                 270

CCG GCC CGT TAT GCG AAC GCA ATG GCA GTC GGA GCT ACT GAC CAA AAC      864
Pro Ala Arg Tyr Ala Asn Ala Met Ala Val Gly Ala Thr Asp Gln Asn
    275                 280                 285

AAC AAC CGC GCC AGC TTT TCA CAG TAT GGC GCA GGG CTT GAC ATT GTC      912
Asn Asn Arg Ala Ser Phe Ser Gln Tyr Gly Ala Gly Leu Asp Ile Val
290                 295                 300

GCA CCA GGT GTA AAC GTG CAG AGC ACA TAC CCA GGT TCA ACG TAT GCC      960
Ala Pro Gly Val Asn Val Gln Ser Thr Tyr Pro Gly Ser Thr Tyr Ala
305                 310                 315                 320

AGC TTA AAC GGT ACA TCG ATG GCT ACT CCT CAT GTT GCA GGT GCA GCA     1008
Ser Leu Asn Gly Thr Ser Met Ala Thr Pro His Val Ala Gly Ala Ala
            325                 330                 335

GCC CTT GTT AAA CAA AAG AAC CCA TCT TGG TCC AAT GTA CAA ATC CGC     1056
Ala Leu Val Lys Gln Lys Asn Pro Ser Trp Ser Asn Val Gln Ile Arg
        340                 345                 350

AAT CAT CTA AAG AAT ACG GCA ACG AGC TTA GGA AGC ACG AAC TTG TAT     1104
Asn His Leu Lys Asn Thr Ala Thr Ser Leu Gly Ser Thr Asn Leu Tyr
    355                 360                 365

GGA AGC GGA CTT GTC AAT GCA GAA GCG GCA ACA CGC                     1140
Gly Ser Gly Leu Val Asn Ala Glu Ala Ala Thr Arg
370                 375                 380

(2) INFORMATION FOR SEQ ID NO:7:

(i) SEQUENCE CHARACTERISTICS:
        (A) LENGTH: 380 amino acids
        (B) TYPE: amino acid
        (D) TOPOLOGY: linear (ii) MOLECULE TYPE: protein (xi) SEQUENCE DESCRIPTION: SEQ ID NO:7:

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala Ala Glu Glu Ala Lys
            20                  25                  30

Glu Lys Tyr Leu Ile Gly Phe Asn Glu Gln Glu Ala Val Ser Glu Phe
        35                  40                  45

Val Glu Gln Val Glu Ala Asn Asp Glu Val Ala Ile Leu Ser Glu Glu
    50                  55                  60

Glu Glu Val Glu Ile Glu Leu Leu His Glu Phe Glu Thr Ile Pro Val
65                  70                  75                  80
```

```
Leu Ser Val Glu Leu Ser Pro Glu Asp Val Asp Ala Leu Glu Leu Asp
                85                  90                  95

Pro Ala Ile Ser Tyr Ile Glu Glu Asp Ala Glu Val Thr Thr Met Ala
            100                 105                 110

Gln Ser Val Pro Trp Gly Ile Ser Arg Val Gln Ala Pro Ala Ala His
            115                 120                 125

Asn Arg Gly Leu Thr Gly Ser Gly Val Lys Val Ala Val Leu Asp Thr
130                 135                 140

Gly Ile Ser Thr His Pro Asp Leu Asn Ile Arg Gly Gly Ala Ser Phe
145                 150                 155                 160

Val Pro Gly Glu Pro Ser Thr Gln Asp Gly Asn Gly His Gly Thr His
                165                 170                 175

Val Ala Gly Thr Ile Ala Ala Leu Asn Asn Ser Ile Gly Val Leu Gly
            180                 185                 190

Val Ala Pro Ser Ala Glu Leu Tyr Ala Val Lys Val Leu Gly Ala Ser
            195                 200                 205

Gly Ser Gly Ser Val Ser Ser Ile Ala Gln Gly Leu Glu Trp Ala Gly
210                 215                 220

Asn Asn Gly Met His Val Ala Asn Leu Ser Leu Gly Ser Pro Ser Pro
225                 230                 235                 240

Ser Ala Thr Leu Glu Gln Ala Val Asn Ser Ala Thr Ser Arg Gly Val
            245                 250                 255

Leu Val Val Ala Ala Ser Gly Asn Ser Gly Ala Gly Ser Ile Ser Tyr
            260                 265                 270

Pro Ala Arg Tyr Ala Asn Ala Met Ala Val Gly Ala Thr Asp Gln Asn
            275                 280                 285

Asn Asn Arg Ala Ser Phe Ser Gln Tyr Gly Ala Gly Leu Asp Ile Val
            290                 295                 300

Ala Pro Gly Val Asn Val Gln Ser Thr Tyr Pro Gly Ser Thr Tyr Ala
305                 310                 315                 320

Ser Leu Asn Gly Thr Ser Met Ala Thr Pro His Val Ala Gly Ala Ala
            325                 330                 335

Ala Leu Val Lys Gln Lys Asn Pro Ser Trp Ser Asn Val Gln Ile Arg
            340                 345                 350

Asn His Leu Lys Asn Thr Ala Thr Ser Leu Gly Ser Thr Asn Leu Tyr
            355                 360                 365

Gly Ser Gly Leu Val Asn Ala Glu Ala Ala Thr Arg
370                 375                 380

(2) INFORMATION FOR SEQ ID NO:8:

(i) SEQUENCE CHARACTERISTICS:
        (A) LENGTH: 1140 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1140

(ix) FEATURE:
        (A) NAME/KEY: mat_peptide
        (B) LOCATION: 334..1140

(xi) SEQUENCE DESCRIPTION: SEQ ID NO:8:

ATG AAG AAA CCG TTG GGG AAA ATT GTC GCA AGC ACC GCA CTA CTC ATT      48
```

-continued

```
Met Lys Lys Pro Leu Gly Lys Ile Val Ala Ser Thr Ala Leu Leu Ile
-111-110         -105              -100
TCT GTT GCT TTT AGT TCA TCG ATC GCA TCG GCT GCT GAA GAA GCA AAA    96
Ser Val Ala Phe Ser Ser Ser Ile Ala Ser Ala Ala Glu Glu Ala Lys
-95              -90              -85              -80
GAA AAA TAT TTA ATT GGC TTT AAT GAG CAG GAA GCT GTC AGT GAG TTT   144
Glu Lys Tyr Leu Ile Gly Phe Asn Glu Gln Glu Ala Val Ser Glu Phe
             -75              -70              -65
GTA GAA CAA GTA GAG GCA AAT GAC GAG GTC GCC ATT CTC TCT GAG GAA   192
Val Glu Gln Val Glu Ala Asn Asp Glu Val Ala Ile Leu Ser Glu Glu
             -60              -55              -50
GAG GAA GTC GAA ATT GAA TTG CTT CAT GAA TTT GAA ACG ATT CCT GTT   240
Glu Glu Val Glu Ile Glu Leu Leu His Glu Phe Glu Thr Ile Pro Val
             -45              -40              -35
TTA TCC GTT GAG TTA AGC CCA GAA GAT GTG GAC GCG CTT GAA CTC GAT   288
Leu Ser Val Glu Leu Ser Pro Glu Asp Val Asp Ala Leu Glu Leu Asp
             -30              -25              -20
CCA GCG ATT TCT TAT ATT GAA GAG GAT GCA GAA GTA ACG ACA ATG GCG   336
Pro Ala Ile Ser Tyr Ile Glu Glu Asp Ala Glu Val Thr Thr Met Ala
-15              -10              -5                    1
CAA TCA GTG CCA TGG GGA ATT AGC CGT GTG CAA GCC CCA GCT GCC CAT   384
Gln Ser Val Pro Trp Gly Ile Ser Arg Val Gln Ala Pro Ala Ala His
              5                  10               15
AAC CGT GGA TTG ACA GGT TCT GGT GTA AAA GTT GCT GTC CTC GAT ACA   432
Asn Arg Gly Leu Thr Gly Ser Gly Val Lys Val Ala Val Leu Asp Thr
         20                  25               30
GGT ATT TCC ACT CAT CCA GAC TTA AAT ATT CGT GGT GGC GCT AGC TTT   480
Gly Ile Ser Thr His Pro Asp Leu Asn Ile Arg Gly Gly Ala Ser Phe
         35               40               45
GTA CCA GGG GAA CCA TCC ACT CAA GAT GGG AAT GGG CAT GGC ACG CAT   528
Val Pro Gly Glu Pro Ser Thr Gln Asp Gly Asn Gly His Gly Thr His
50               55               60               65
GTG GCC GGG ACG ATT GCT GCT TTA GAC AAC TCG ATT GGC GTT CTT GGC   576
Val Ala Gly Thr Ile Ala Ala Leu Asp Asn Ser Ile Gly Val Leu Gly
                 70               75               80
GTA GCG CCG AGC GCG GAA CTA TAC GCT GTT AAA GTA TTA GGG GCG AGC   624
Val Ala Pro Ser Ala Glu Leu Tyr Ala Val Lys Val Leu Gly Ala Ser
             85               90               95
GGT TCA GGC GCC ATC AGC TCG ATT GCC CAA GGA TTG GAA TGG GCA GGG   672
Gly Ser Gly Ala Ile Ser Ser Ile Ala Gln Gly Leu Glu Trp Ala Gly
         100              105              110
AAC AAT GGC ATG CAC GTT GCT AAT TTG AGT TTA GGA AGC CCT TCG CCA   720
Asn Asn Gly Met His Val Ala Asn Leu Ser Leu Gly Ser Pro Ser Pro
         115              120              125
AGT GCC ACA CTT GAG CAA GCT GTT AAT AGC GCG ACT TCT AGA GGC GTT   768
Ser Ala Thr Leu Glu Gln Ala Val Asn Ser Ala Thr Ser Arg Gly Val
130              135              140              145
CTT GTT GTA GCG GCA TCT GGG AAT GAA GGT GCA GGC TCA ATC GAC TAT   816
Leu Val Val Ala Ala Ser Gly Asn Glu Gly Ala Gly Ser Ile Asp Tyr
                 150              155              160
CCG GCC CGT TAT GCG AAC GCA ATG GCA GTC GGA GCT ACT GAC CAA AAC   864
Pro Ala Arg Tyr Ala Asn Ala Met Ala Val Gly Ala Thr Asp Gln Asn
         165              170              175
AAC AAC CGC GCC AGC TTT TCA CAG TAT GGC GCA GGG CTT GAC ATT GTC   912
Asn Asn Arg Ala Ser Phe Ser Gln Tyr Gly Ala Gly Leu Asp Ile Val
         180              185              190
GCA CCA GGT GTA AAC GTG CAG AGC ACA TAC CCA ATT TCA ACG TAT GCC   960
Ala Pro Gly Val Asn Val Gln Ser Thr Tyr Pro Ile Ser Thr Tyr Ala
195              200              205
```

```
AGC TTA AAC GGT ACA TCG ATG GCT ACT CCT CAT GTT GCA GGT GCA GCA      1008
Ser Leu Asn Gly Thr Ser Met Ala Thr Pro His Val Ala Gly Ala Ala
210                 215                 220                 225

GCC CTT GTT AAA CAA AAG AAC CCA TCT TGG TCC AAT GTA CAA ATC CGC      1056
Ala Leu Val Lys Gln Lys Asn Pro Ser Trp Ser Asn Val Gln Ile Arg
            230                 235                 240

AAT CAT CTA AAG AAT ACG GCA ACG AGC TTA GGA AGC ACG AAC TTG TAT      1104
Asn His Leu Lys Asn Thr Ala Thr Ser Leu Gly Ser Thr Asn Leu Tyr
                245                 250                 255

GGA AGC GGA CTT GTC AAT GCA GAA GCG GCA ACA CGC                      1140
Gly Ser Gly Leu Val Asn Ala Glu Ala Ala Thr Arg
            260                 265
```

(2) INFORMATION FOR SEQ ID NO:9:

(i) SEQUENCE CHARACTERISTICS:
       (A) LENGTH: 380 amino acids
       (B) TYPE: amino acid
       (D) TOPOLOGY: linear (ii) MOLECULE TYPE: protein (xi) SEQUENCE DESCRIPTION: SEQ ID NO:9:

```
Met Lys Lys Pro Leu Gly Lys Ile Val Ala Ser Thr Ala Leu Leu Ile
-111 -110           -105             -100

Ser Val Ala Phe Ser Ser Ser Ile Ala Ser Ala Ala Glu Glu Ala Lys
-95             -90              -85                      -80

Glu Lys Tyr Leu Ile Gly Phe Asn Glu Gln Glu Ala Val Ser Glu Phe
                -75             -70                      -65

Val Glu Gln Val Glu Ala Asn Asp Glu Val Ala Ile Leu Ser Glu Glu
            -60              -55                      -50

Glu Glu Val Glu Ile Glu Leu Leu His Glu Phe Glu Thr Ile Pro Val
        -45                  -40              -35

Leu Ser Val Glu Leu Ser Pro Glu Asp Val Asp Ala Leu Glu Leu Asp
        -30                  -25              -20

Pro Ala Ile Ser Tyr Ile Glu Glu Asp Ala Glu Val Thr Thr Met Ala
-15             -10              -5                        1

Gln Ser Val Pro Trp Gly Ile Ser Arg Val Gln Ala Pro Ala Ala His
                5                   10              15

Asn Arg Gly Leu Thr Gly Ser Gly Val Lys Val Ala Val Leu Asp Thr
            20                  25              30

Gly Ile Ser Thr His Pro Asp Leu Asn Ile Arg Gly Gly Ala Ser Phe
        35                  40                  45

Val Pro Gly Glu Pro Ser Thr Gln Asp Gly Asn Gly His Gly Thr His
50              55                  60                  65

Val Ala Gly Thr Ile Ala Ala Leu Asp Asn Ser Ile Gly Val Leu Gly
                70                  75                  80

Val Ala Pro Ser Ala Glu Leu Tyr Ala Val Lys Val Leu Gly Ala Ser
            85                  90                  95

Gly Ser Gly Ala Ile Ser Ser Ile Ala Gln Gly Leu Glu Trp Ala Gly
            100                 105                 110

Asn Asn Gly Met His Val Ala Asn Leu Ser Leu Gly Ser Pro Ser Pro
115                 120                 125

Ser Ala Thr Leu Glu Gln Ala Val Asn Ser Ala Thr Ser Arg Gly Val
130                 135                 140                 145

Leu Val Val Ala Ala Ser Gly Asn Glu Gly Ala Gly Ser Ile Asp Tyr
                150                 155                 160
```

```
-continued

Pro Ala Arg Tyr Ala Asn Ala Met Ala Val Gly Ala Thr Asp Gln Asn
            165             170             175

Asn Asn Arg Ala Ser Phe Ser Gln Tyr Gly Ala Gly Leu Asp Ile Val
            180             185             190

Ala Pro Gly Val Asn Val Gln Ser Thr Tyr Pro Ile Ser Thr Tyr Ala
    195             200             205

Ser Leu Asn Gly Thr Ser Met Ala Thr Pro His Val Ala Gly Ala Ala
210             215             220             225

Ala Leu Val Lys Gln Lys Asn Pro Ser Trp Ser Asn Val Gln Ile Arg
            230             235             240

Asn His Leu Lys Asn Thr Ala Thr Ser Leu Gly Ser Thr Asn Leu Tyr
            245             250             255

Gly Ser Gly Leu Val Asn Ala Glu Ala Ala Thr Arg
        260             265
```